(12) United States Patent
Gebert et al.

(10) Patent No.: US 9,894,917 B2
(45) Date of Patent: Feb. 20, 2018

(54) GLYCOSYLATION AS A STABILIZER FOR PHYTASE

(71) Applicant: Danisco US Inc., Palo Alto, CA (US)

(72) Inventors: Mark S. Gebert, Pacifica, CA (US); Sang-Kyu Lee, Palo Alto, CA (US); Mariliz Johnson, San Mateo, CA (US); Michael Ward, San Francisco, CA (US)

(73) Assignee: DANISCO US INCCA (US)

( * ) Notice: Subject to any disclaimer, the term of this patent is extended or adjusted under 35 U.S.C. 154(b) by 82 days.

(21) Appl. No.: 14/377,134

(22) PCT Filed: Feb. 1, 2013

(86) PCT No.: PCT/US2013/024415
§ 371 (c)(1),
(2) Date: Aug. 6, 2014

(87) PCT Pub. No.: WO2013/119470
PCT Pub. Date: Aug. 15, 2013

(65) Prior Publication Data
US 2015/0030717 A1 Jan. 29, 2015

Related U.S. Application Data

(60) Provisional application No. 61/595,941, filed on Feb. 7, 2012.

(51) Int. Cl.
*C12N 9/16* (2006.01)
*A23K 1/165* (2006.01)
(Continued)

(52) U.S. Cl.
CPC .......... *A23K 1/1653* (2013.01); *A23K 20/147* (2016.05); *A23K 20/189* (2016.05);
(Continued)

(58) Field of Classification Search
None
See application file for complete search history.

(56) References Cited

U.S. PATENT DOCUMENTS 4,689,297 A 8/1987 Good et al.
5,324,649 A 6/1994 Arnold et al.
(Continued)

FOREIGN PATENT DOCUMENTS

EP 0656058 B1 6/1995
EP 0804532 11/1997
(Continued)

OTHER PUBLICATIONS

GenBank Accession No. AAQ90419.1, published Jan. 5, 2005.*
(Continued)

*Primary Examiner* — Robert Mondesi
*Assistant Examiner* — Richard Ekstrom

(57) ABSTRACT

The present teachings provide modified enzymes, preferably phytases, which have increased stability, hypothesized to arise from increased glycosylation. The enzymes can be modified to introduce or increase the number of glycosylation sites in the amino acid sequence, or glycosylation can be increased by the use of specific host production methods, or both. The enzymes of the present teachings have an increased stability after treatment at elevated temperature, which can be measured by inactivity reversibility or percent recovery following a treatment such as heating. The enzymes of the present teachings find application for example in food, feed, and feed pelleting.

16 Claims, 4 Drawing Sheets

(51) Int. Cl.
 *A23K 20/147* (2016.01)
 *A23K 20/189* (2016.01)
(52) U.S. Cl.
 CPC ........ *C12N 9/16* (2013.01); *C12Y 301/03008* (2013.01); *C12Y 301/03026* (2013.01); *C12Y 301/03* (2013.01)

(56) References Cited

U.S. PATENT DOCUMENTS

| | | | |
|---|---|---|---|
| 5,739,091 | A | 4/1998 | Kiesser et al. |
| 6,110,719 | A | 8/2000 | Kretz |
| 6,248,706 | B1 | 6/2001 | Herrmann et al. |
| 6,534,466 | B2 | 3/2003 | Christensen, Jr. |
| 2005/0281792 | A1 | 12/2005 | Short et al. |
| 2009/0098249 | A1* | 4/2009 | Cervin ............... C12N 9/16 426/61 |
| 2010/0124586 | A1 | 5/2010 | Becker et al. |

FOREIGN PATENT DOCUMENTS

| | | | |
|---|---|---|---|
| WO | 9932595 A1 | 7/1999 | |
| WO | 0190333 A2 | 11/2001 | |
| WO | 2004035070 A1 | 4/2004 | |
| WO | 2005001036 A2 | 1/2005 | |
| WO | 2006028684 A2 | 3/2006 | |
| WO | 2006043178 A2 | 4/2006 | |
| WO | WO 2006043178 A2 * | 4/2006 | |
| WO | 2006050584 A1 | 5/2006 | |
| WO | 2007044968 A2 | 4/2007 | |
| WO | 2008039370 A1 | 4/2008 | |
| WO | 2008092901 A2 | 8/2008 | |
| WO | 2008097619 A2 | 8/2008 | |
| WO | 2009129489 A2 | 10/2009 | |
| WO | 2010120471 A2 | 10/2009 | |
| WO | 2011117397 A1 | 9/2011 | |

OTHER PUBLICATIONS

GenBank Accession No. ABX80238.1, published Apr. 20, 2008.*
International Search Report, PCT Application No. PCT/US2013/024415, Filed February 1, 2013.
Berka et al., Molecular Characterization and Expression of a Phytase Gene From the Thermophilic Fungus Thermomyces Lanuginosus, Applied and Environmental Microbiology, vol. 64, No. 11 (1998), pp. 4423-4427.
Engelen et al., Dtermination of Phytase Activity in Feed by a Colorimetric Enzymatic Method: Collaborative Interlaboratory Study, Journal of AOAC International., vol. 84, No. 3 (2001), pp. 629-633.
Kerovuo et al., Isolation, Characterization, Molecular Gene Cloning and Sequencing of a Novel Phytase From *Bacillus subtilis*, Applied and Environmental Microbiology, vol, 64, No. 6 (1998), pp. 2079-2085.
Kim et al.. Isolation and Characterization of a Phytase With Improved Properties From Citrobacter. Braakii, Biotechnology Letters, vol. 25 (2003), pp. 1231-1234.
Lassen et al., Expression, Gene Cloning and Characterization of Five Novel Phytases From Four Basidiomycete Fungi: *Peniophora lycii, Agrocybe pediades,A Ceriporia Sp.*, and *Trametes pubescens*, Applied and Environmental Microbiology, vol. 67, No. 10 (2001), pp. 4701-4707.
Penttila et al., A Versatile Transformation System for the Cellulolytic Filamentous Fungus *Trichoderma Reesei*, Gene, vol. 61 (1987), pp. 155-164.
Stals et al.. Identification of a Gene Coding for a Deglycosylating Enzyme in Hypocrea Jecorina, Fems Microbiol Lett, vol. 303 (2010), pp. 9-17.
Weerapana et al., Reviewasparagine-Linked Protein Glycosylation: From Eukaryotic to Prokaryotic Systems, Glycobiology, vol. 16, No. 6 (2006) pp. 91R-101R.
Wodzinski et al., Phytase - Thirty+ Years of Basic and Applied Scientific Research Necessary to Generate a Product, Adv Appl Microbiol, vol. 42 (1996), pp. 263-302.
Wyss et al.. Comparison of the Thermostability Properties of Three Acid Phosphatases From Molds: Aspergillus Fumigatus Phytase, A Niger Phytase, and A Niger PH 2.5 Acid Phosphatase, Applied and Environmental Microbiology, vol. 64, No. 11 (1998), pp. 4446-4451.
Wyss et al., Biochemical Characterization of Fungal Phytases (Myo-Inositol Hexakisphsphate Phosphohydrolases): Catalytic Properties, Applied and Environmental Microbiology, vol. 65, No. 2 (1999), pp. 367-373.
Yoon et al., Isolation and Identification of Phytase-Producing Bacterium, Entrobacter Sp. 4, and Enzymatic Properties of Phytase Enzyme, Enzyme and Micronial Technology, vol. 18 (1996), pp. 283-290.
Zinn et al., Gene Cloning, Expression and Characterization of Novel Phytase From Obesumbacterium Proteus, Fems Microbiology Letters, vol. 236 (2004), pp. 283-290.
Fairfield, D., McEllhiney, Editor, Chapter 10, Pelleting Cost Center, In Feed Manufacturing Technology IV, American Feed Industry Association, Arlington, VA (1994) pp. 110-139.

* cited by examiner

GLYCOSYLATION AS A STABILIZER FOR PHYTASE

CROSS REFERENCE TO RELATED APPLICATIONS

The present application is a 371 National Stage application of PCT/US2013/24415, filed on Feb. 1, 2013, which claims priority to U.S. Provisional Application Ser. No. 61/595,941, filed on Feb. 7, 2012, which are hereby incorporated by reference in their entirety.

SEQUENCE LISTING

The sequence listing submitted via EFS, in compliance with 37 C.F.R. § 1.52(e), is incorporated herein by reference. The sequence listing text file submitted via EFS contains the file "31475WO_104120_00061-ST25.txt" created on Mar. 1, 2013, which is 50,000 bytes in size.

TECHNICAL FIELD

The present teachings relate to the field of modified phytases. More specifically, the present teachings relate to the glycosylation of phytases through mutation of the phytases themselves and/or due to phytase production methods involving deglycosylation-defective host cells. In some embodiments the phytases concerned are fungal or bacterial, and can be from *Buttiauxella*.

BACKGROUND

Phytate is the major storage form of phosphorus in cereals and legumes. However, monogastric animals such as pig, poultry and fish are not able to metabolise or absorb phytate (or phytic acid) and therefore it is excreted, leading to potential phosphorous pollution in areas of intense livestock production. Moreover, phytic acid also acts as an antinutritional agent in monogastric animals by chelating metal agents such as calcium, copper and zinc.

In order to provide sufficient phosphates for growth and health of these animals, inorganic phosphate is added to their diets. Such addition can be costly and further increases potential pollution problems.

Through the action of phytase, phytate is generally hydrolysed to give lower inositol-phosphates and inorganic phosphate. Phytases are useful as additives to animal feeds where they improve the availability of organic phosphorus to the animal and decrease phosphate pollution of the environment (Wodzinski R J, Ullah A H. Adv Appl Microbiol. 42, 263-302 (1996)).

A number of phytases of fungal origin (Wyss M. et al. Appl. Environ. Microbiol. 65 (2), 367-373 (1999); Berka R. M. et al. Appl. Environ. Microbiol. 64 (II), 4423-4427 (1998); Lassen S. et al. Appl. Environ. Microbiol. 67 (10), 4701-4707 (2001)) and bacterial origin (Greiner R. et al. Arch. Biochem. Biophys. 303 (I), 107-113 (193); Kerovuo et al. Appl. Environ. Microbiol. 64 (6), 2079-2085 (1998); Kim H. W. et al. Biotechnol. Lett. 25, 1231-1234 (2003); Greiner R. et al. Arch. Biochem. Biophys. 341 (2), 201-206 (1997); Yoon S. J. et al. Enzyme and microbial technol. 18, 449-454 (1996); Zinin N. V. et al. FEMS Microbiol. Lett. 236, 283-290 (2004)) have been described in the literature. Specifically BP11 (WO2006/043178), BP17 (WO2008/097619) and BP111 (WO2009/129489) are known variant phytases suitable for use in food and animal feed due to their stability, especially their thermal stability. These phytases are variants of the wild-type phytase of *Buttiauxella* P1-29 (deposited under accession number NCIMB 4124). Phytase is known to undergo reversible thermal inactivation (Wyss, Appl. Envir. Microbiol. (1998) 64:4446).

Animal feeds may be made, produced and processed at high temperatures. In particular they may be formed by pellets or granules such as those described in WO99/32595 and WO2007/044968. Production of animal feeds therefore requires the feeds and feed ingredients to be thermostable at high temperatures. It is therefore advantageous if a feed enzyme, particularly phytase, retains a high level of enzymatic activity after exposure to high or elevated temperatures.

Enzymes may be modified at the amino acid level to introduce glycosylation sites, which promote the glycosylation of the enzyme. For example, an N-linked glycan is attached to the asparagine residue within the motif NXS/T on the surface of a secreted protein (Weerapana and Imperiali (2006) Glycobiology 16:91 R-101R). It is known that glycosylation of an enzyme can provide increased thermostability (Koseki et al. (2006) Biosci. Biotechnol. Biochem. 70: 2476-2480). It is also known that increased glycosylation can increase the protease stability at low pH of some phytases (WO01/90333) as well as thermostability (WO2006/028684). However, these references do not disclose phytase of Butiiauxella origin, or that further increased glycosylation improves resistance to the steam treatment during feed pelleting when the enzyme is in solid state.

The present teachings provide improved glycosylated phytases with increased inactivity reversibility. In some embodiments, the phytases can be used in food or feed. In some embodiments, the phytases undergo a pelleting process for inclusion in the food or feed.

SUMMARY

In some embodiments, the present teachings provide a phytase polypeptide comprising SEQ ID NO: 1 and variants at least 75%, 85%, 90%, 95%, 98%, 99%, or 99.9% identical thereto, comprising increased glycosylation and increased stability.

In some embodiments, the present teachings provide a phytase polypeptide comprising SEQ ID NO:1 and variants at least 75%, 85%, 90%, 95%, 98%, 99%, or 99.9% identical thereto, wherein the phytase polypeptide is produced in a deglycosylation-deficient host.

In some embodiments, the present teachings provide a phytase polypeptide comprising SEQ ID NO: 1 and variants at least 75%, 85%, 90%, 95%, 98%, 99%, or 99.9% identical thereto, comprising at least one additional glycosylation site, wherein the at least one additional glycosylation site is achieved by introducing amino acid changes to create an N-linked glycosylation site motif Asn-Xaa-Ser/Thr, where Xaa can be any amino acid.

In some embodiments, the present teachings provide a phytase polypeptide produced in a deglyosylation-deficient host.

In some embodiments, the present teachings provide a phytase polypeptide having at least 75%, 85%, 90%, 95%, 98%, 99%, or 99.9% identity to any of SEQ ID NOs 1, 2, 3, 4, 5, 6, 7, 8, 9, 10, or 11.

In some embodiments, the present teachings provide a method for increasing the stability of a pelleted phytase polypeptide comprising; glycosylating a phytase polypeptide; forming a granule with the phytase polypeptide; pelleting the granule at a temperature of at least 85 C, at least 90 C, or at least 95 C, to form a pelleted phytase polypeptide;

and, increasing the stability of the pelleted phytase polypeptide as compared to a control pelleted phytase polypeptide lacking the glycosylating.

In some embodiments, the present teachings provide a method of making food or feed with high phytase activity, In some embodiments, the present teachings provide a method for feeding animals comprising administering a feed composition comprising a phytase polypeptide.

In some embodiments, the present teachings provide a phytase polypeptide produced by the methods herein.

In some embodiments, the present teachings provide a nucleic acid encoding a phytase polypeptide.

In some embodiments, the present teachings provide a vector or host cell comprising a nucleic acid sequence.

DESCRIPTION OF THE FIGURES

The present teachings will be described by reference to the following Figures.

SEQUENCES

Figure 1:
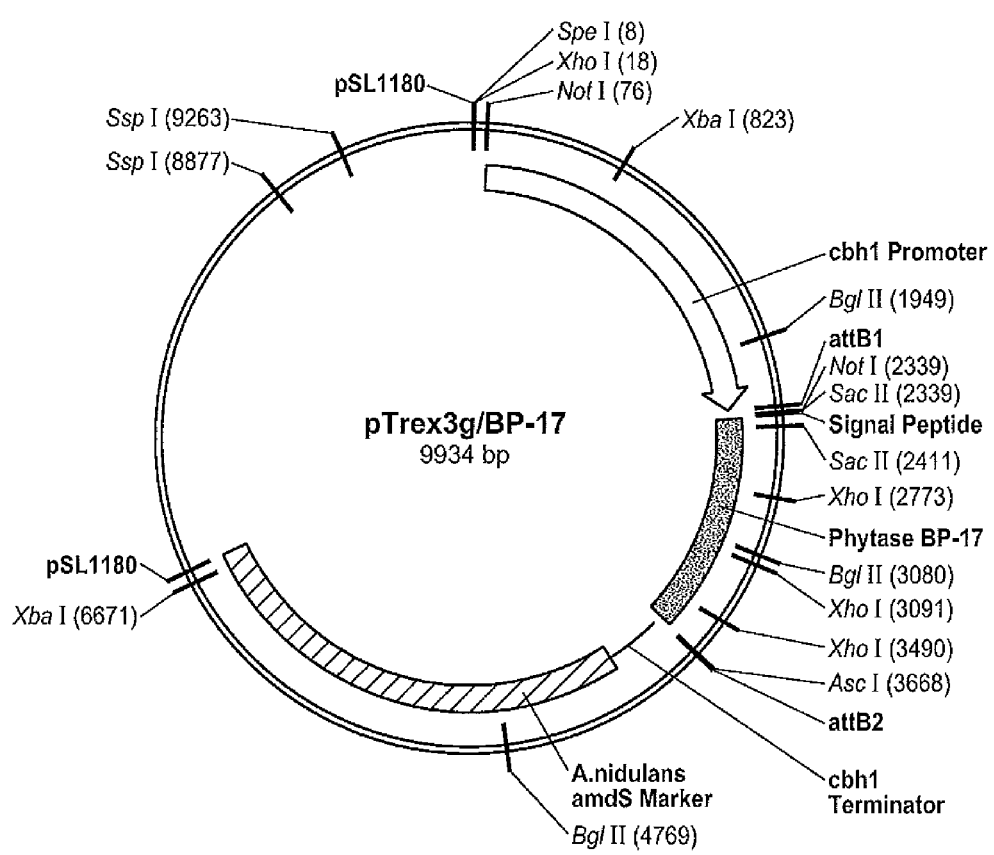
FIG. 1 provides a map of Plasmid pTrex3g/BP-17.

SEQ ID NO:1=BP17, a variant phytase comprising 12 amino acid substitutions compared to the wild type (SEQ ID NO:4), lacking the signal sequence (SEQ ID NO:12)

SEQ ID NO:2=BP11, a variant phytase comprising 11 amino acid substitutions compared to the wild type (SEQ ID NO:4), lacking the signal sequence (SEQ ID NO:12).

SEQ ID NO:3=BP111, a variant phytase comprising 21 amino acid substitutions compared to the wild type (SEQ ID NO:4), lacking the signal sequence (SEQ ID NO:12).

SEQ ID NO:4=wild type phytase encoded by *Buttiauxella* sp. strain P 1-29 deposited under accession number NCIMB 41248, lacking the signal sequence (SEQ ID NO:12).

SEQ ID NO:5=BP17 with an additional amino acid substitution E121T.

SEQ ID NO:6=BP17 with an additional amino acid substitution P394N.

SEQ ID NO:7=BP17 with an additional amino acid substitution D386N.

SEQ ID NO:8=BP17 with additional amino acid substitutions K202N and N204T.

SEQ ID NO:9=BP17 with additional amino acid substitutions Q151N and P153S.

SEQ ID NO:10=BP17 with an additional amino acid substitution P373T.

SEQ ID NO:11=BP17 with an additional amino acid substitution Q76N.

SEQ ID NO:12=signal sequence for wild type (SEQ ID NO:4).

SEQ ID NO:13=DNA sequence of BP-17 variant of *Buttiauxella* phytase containing a SpeI site at the 5' end, and AscI site at the 3' end.

SEQ ID NOs:14-17=primers.

SEQ ID NO:18=PCR product sequence in Example 1, between the cbh1 promoter and the signal sequence/BP-17 coding sequence.

SEQ ID NO:19=PCR product sequence in Example 1, between the 3' end of the BP-17 coding sequence and the cbh1 terminator region.

SEQ ID NOs:20-29=primers.

SEQ ID NOs:30-47=primers.

DETAILED DESCRIPTION

The practice of the present teachings will employ, unless otherwise indicated, conventional techniques of molecular biology (including recombinant techniques), microbiology, cell biology, biochemistry, and animal feed pelleting, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); *Gene Transfer and Expression: A Laboratory Manual* (Kriegler, 1990), and Fairfield, D. 1994. Chapter 10, Pelleting Cost Center. In Feed Manufacturing Technology IV. (McEllhiney, editor), American Feed Industry Association, Arlington, Va., pp. 110-139.

Unless defined otherwise herein, all technical and scientific terms used herein have the same meaning as commonly understood by one of ordinary skill in the art to which the present teachings belong. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present teachings.

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

By "homologue" shall mean an entity having a specified degree of identity with the subject amino acid sequences and the subject nucleotide sequences. A homologous sequence is taken to include an amino acid sequence that is at least 75%, 80%, 85%, 86%, 87%, 88%, 89%, 90%, 91%, 92%, 93%, 94%, 95%, 96%, 97%, 98% or even 99% identical to the subject sequence, using the conventional sequence alignment tool Clustal V with default parameters. Typically, homologues will include the same active site residues as the subject amino acid sequence, though may include any number of conservative amino acid substitutions. Exemplary conservative amino acid substitutions are listed in the following Table of Conservative Amino Acid Substitutions.

Conservative Amino Acid Substitutions

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

As used herein, the term "phytase" means a protein or polypeptide which is capable of catalysing the hydrolysis of esters of phosphoric acid, including phytate/phytic acid, and releasing inorganic phosphate. Illustrative phytases are discussed and referenced throughout the present teachings, and includes *E. Coli* phytase (U.S. Pat. No. 6,110,719), and those obtained from any of a variety of sources, including *Ascomycetes, Aspergillus awamori, Aspergillus niger, Thermomyces, Humicola, Basidiomycetes, Bacillus subtilis*, and *Schwannniomyces occidentalis*. Some phytases in addition to phytate are capable of hydrolysing at least some of the inositol-phosphates of intermediate degrees of phosphorylation. In one embodiment, the active enzyme produced or modified in the present teachings is a 6-phytase. The 6-phytase is also called "4-phytase" or "phytate 6-phosphatase". Further phytases include histidine acid phytases (HAP), which is a group comprising members found among prokaryotes (e.g. appA phytase from *Escherichia coli*) and eukaryotes (phyA and B from *Aspergillus* sp., HAP phytases from yeast and plants. HAP phytases share a common active site motif, RHGXRXP, at the N-terminal end and a HD motif at the C-terminal end in their DNA sequences."

The present phytases may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective phytase polypeptides. The present amylase polypeptides may also be truncated to remove the N or C-termini, so long as the resulting polypeptides retain phytase activity.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The term "variant," with respect to a polypeptide, refers to a polypeptide that differs from a specified wild-type, parental, or reference polypeptide in that it includes a man-made substitution, insertion, or deletion at one or more amino acid positions. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes at different levels or under different conditions than found in nature.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., a phytase) has been introduced. Exemplary host strains are *Trichoderma* sp. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobial resistance (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences that control termination of transcription and translation.

The term "operably linked" means that specified components are in a relationship (including but not limited to juxtaposition) permitting them to function in an intended manner. For example, a regulatory sequence is operably linked to a coding sequence if the expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Filamentous fungi" refers to all filamentous forms of the subdivision Eumycotina and Oomycota (See, Alexopoulos, C. J. (1962), *Introductory Mycology*, Wiley, New York). These fungi are characterized by a vegetative mycelium with a cell wall composed of chitin, cellulose, and other complex polysaccharides. The filamentous fungi of the present teachings are morphologically, physiologically, and genetically distinct from yeasts. Vegetative growth by filamentous fungi is by hyphal elongation and carbon catabolism is obligatorily aerobic. In the present teachings, the filamentous fungal parent cell may be a cell of a species of *Trichoderma*, e.g., *Trichoderma reesei* (previously classified as *T. longibrachiatum* and currently also known as *Hypocrea jecorina*), *Trichoderma viride*, *Trichoderma koningii*, or *Trichoderma harzianum*. Additional filamentous fungi include *Aspergillus*, *Fusarium*, *Chrysosporium*, *Penicillium*, *Humicola*, *Neurospora*, *Myceliophthora*, or alternative sexual forms thereof such as *Emericella*, *Hypocrea*.

The terms "isolated" and "separated" refer to a compound, protein (polypeptides), cell, nucleic acid, amino acid, or other specified material or component that is removed from at least one other material or component with which it is naturally associated as found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

As used herein, the terms "modification" and "alteration" are used interchangeably and mean to change or vary. In the context of modifying or altering a polypeptide, these terms may mean to change the amino acid sequence, either directly or by changing the encoding nucleic acid, or to change the structure of the polypeptide such as by glycosylating the enzyme.

The term "glycosylation" as used herein refers to the attachment of glycans to molecules, for example to proteins. Glycosylation may be an enzymatic reaction. The attachment formed may be through covalent bonds. The phrase "highly glycosylated" refers to a molecule such as an enzyme which is glycosylated at all or nearly all of the available glycosylation sites, for instance N-linked glycosylation sites.

The term "glycan" as used herein refers to a polysaccharide or oligosaccharide, or the carbohydrate section of a glycoconjugate such as a glycoprotein. Glycans may be homo- or heteropolymers of monosaccharide residues. They may be linear or branched molecules.

As used herein, the "apparent melting temperature" can be measured by incubating enzyme at a variety of temperatures for a certain time. The remaining activity is then measured at an appropriate assay temperature for the enzyme. Results are plotted on a graph. The incubation temperature that causes 50% loss of residual activity is calculated as the apparent melting temperature.

A "feed" and a "food," respectively, means any natural or artificial diet, meal or the like or components of such meals intended or suitable for being eaten, taken in, digested, by a non-human animal and a human being, respectively.

As used herein, the term "food" is used in a broad sense—and covers food and food products for humans as well as food for non-human animals (i.e. a feed).

The term "feed" is used with reference to products that are fed to animals in the rearing of livestock. The terms "feed" and "animal feed" are used interchangeably. In a preferred embodiment, the food or feed is for consumption by non-ruminants and ruminants. Examples of ruminants include cows, sheep, goats and horses. Examples of non-ruminant animals include mono-gastric animals such as pigs, poultry (such as chickens and turkeys), fish (such as salmon), dogs, cats, and humans.

The food or feed may be in the form of a solution or as a solid—depending on the use and/or the mode of application and/or the mode of administration. In some embodiments, the enzymes mentioned herein may be used as—or in the preparation or production of—a food or feed substance.

As used herein the term "food or feed ingredient" includes a formulation, which is or can be added to foods or foodstuffs and includes formulations which can be used at low levels in a wide variety of products. The food ingredient may be in the form of a solution or as a solid—depending on the use and/or the mode of application and/or the mode of administration. The enzymes described herein may be used as a food or feed ingredient or in the preparation or production. The enzymes may be—or may be added to—food supplements. Feed compositions for monogastric animals typically include compositions comprising plant products which contain phytate. Such compositions include cornmeal, soybean meal, rapeseed meal, cottonseed meal, maize, wheat, barley and sorghum-based feeds. The enzymes described herein may be—or may be added to—foods or feed substances and compositions.

Feed compositions for monogastric animals typically include composition comprising plant products which contain phytate. Such compositions include cornmeal, soybean meal, rapeseed meal, cottonseed meal, maize, wheat, barley and sorghum-based feeds. The enzymes described herein may be—or may be added to foods or feed substances and compositions.

The present teachings also provide a method of preparing a food or a feed ingredient or supplement, the method comprising admixing or adding the enzymes produced by the process of the present description, or modified enzymes of the description, or a composition comprising enzymes according to the present description with another food ingredient. The method for preparing a feed or a food ingredient is also another embodiment of the present description. Such methods may involve pelleting. To prepare a food or feed ingredient, the enzymes of the description can be added in the form of a solid, a formulation such as a pre-mix, or a liquid.

As used herein, the terms "pelleting" and "pellet" refer to the production or use of pellets which are solid, rounded, spherical and cylindrical tablets, particularly feed pellets and solid, extruded animal feed. One example of a known feed pelleting manufacturing process generally includes admixing together food or feed ingredients for about 1 to about 5 minutes at room temperature, transferring the admixture to a surge bin, conveying the admixture to a steam conditioner, optionally transferring the steam conditioned admixture to an expander, transferring the admixture to the pellet mill or extruder, and finally transferring the pellets into a pellet cooler. Fairfield, D. 1994. Chapter 10, Pelleting Cost Center. In Feed Manufacturing Technology IV. (McEllhiney, editor), American Feed Industry Association, Arlington, Va., pp. 110-139.

The term "pellet" refers to a composition of animal feed (usually derived from grain) that has been subjected to a heat treatment, such as a steam treatment, and extruded through a machine. The pellet may incorporate enzyme in the form of granules. The term "granule" is used for particles composed enzymes and other chemicals such as salts and sugars, and may be formed using any of a variety of techniques, including fluid bed granulation approaches to form layered granules.

"NCIMB" is the name of a depository for organisms located in Aberdeen, Scotland named The National Collection of Industrial, food, and Marine Bacteria.

"A," "an" and "the" include plural references unless the context clearly dictates otherwise.

As used herein, "Endo glucosaminidase" (or endoglycosidase, endo glucosaminidase, endo N-acetyl glucosaminidase, ENGase) is a secreted enzyme which removes N-linked glycosylation from other proteins such as phytases (Stals et al. (2010) FEMS Microbiol. Lett. 303:9-17 As used herein, "ETD" indicates that the enzyme is produced in a host having the endo-N-acetyl glucosaminidase gene deleted.

As used herein, the term "stability" refers to any of a variety of effects in which the enzymatic activity or other functional property of a phytase enzyme is beneficially maintained or improved. A phytase can exhibit stability by showing any of improved "recovered activity," "thermostability", and/or "inactivity reversibility."

As used herein, the term "recovered activity" refers to the ratio of (i) the activity of a phytase after treatment (involving one or more of the following stressors: heating, increased pressure, increased pH, decreased pH, storage, drying, exposure to surfactant(s), exposure to solvent(s), and mechanical stress) to (ii) the activity of the phytase before the treatment. The recovered activity may be expressed as a percentage.

The percent recovered activity is calculated as follows:

$$\% \text{ recovered activity} = \left(\frac{\text{activity after treatment}}{\text{activity before treatment}}\right) \times 100\%$$

In the context of pelleting experiments, the "activity before treatment" can be approximated by measuring the phytase activity present in the mash that does not undergo treatment in a manner that is otherwise matched to the phytase that does undergo treatment. For example, the phytase in the untreated mash is handled and stored for a similar time and under similar conditions as the phytase in the treated mash, to control for possible interactions or other effects outside of the specified treatment per se.

As used herein, the term "inactivity reversibility" is a kind of stability that refers to the ability of enzymes exposed to elevated temperatures, for example above 70 C, above 80 C, above 90 C, or above 95 C, to regain some activity and show at least partial reversal of heat-mediated inactivation. The recovery of activity occurs after the elevated temperature is removed. An inactivity reversibility assay is discussed in greater detail in Example 5.

As used herein, the term "control phytase" in conjunction with a phytase refers to the same kind of phytase molecule (e.g. BP17 phytase) as that which has a stabilizing agent added (e.g.—glycosylation by expression in a deglycosylation-deficient host), except that the stabilizing agent was lacking. For example, in one sample phytase BP17 is stabilized by expression in a deglycosylation deficient host and in the comparative control phytase sample the only difference is that the phytase BP 17 was not expressed in the deglycosylation deficient host, such a phytase being a "control phytase".

As used herein, a "unit of phytase activity" is the amount of enzyme which is able to release 1 µmol phosphate per minute. Phytase activity is assayed according to AOAC (Association of Analytical Chemists) Official Method 2000.12, as described in "Determination of phytase activity in feed by a colorimetric enzymatic method: collaborative interlaboratory study" Engelen A J, van der Heeft F C, Randsdorp P H, Somers W A, Schaefer J, van der Vat B J. J AOAC Int. 2001 May-June; 84(3):629-33. Briefly, the ground samples are extracted in 220 mM sodium acetate trihydrate, 68.4 mM calcium chloride dehydrate, 0.01% Tween 20, pH 5.5. The supernatant is then assayed. The assay measures the release of inorganic phosphate from rice phytase, at pH 5.5, for 60 min at 37 C. The assay is stopped with acidic molybdate/vanadate reagent, and phosphate is quantified by intensity of yellow colored complex of the vanadomolybdophosphor.

The following hypothetical experiment is provided to further illustrate and explain the terminology of the present teachings. Here, the units in the table are for convenience depicted as commencing with 100 arbitrary units of phytase activity pre-pelleting. First, looking at the top row of data, for a given control phytase composition such as natively-expressed BP17, the "percent recovered activity" is 50% after the pelleting treatment. Second, looking at the bottom row of data, for a given phytase composition such as endo T-delete expressed BP17, the "percent recovered activity" of the phytase after the pelleting treatment is 80%. Third, looking at the far right column, endo T delete-expressed BP17 phytase has a phytase activity that is 60% higher (80−50=30; 30/50=0.6=60%) as compared to the "control phytase" that was not expressed in the endo T delete expression host. In some embodiments, these improvements can be accompanied by improvements in thermostability, for example as measured by Tm. In some embodiments, these improvements can be accompanied by improvements in inactivity reversibility.

|  | Pre-Pelleting | Post-Pelleting |
|---|---|---|
| Control BP17-native | 100 | 50 |
| Stabilized BP17-EDT | 100 | 80 |

Exemplary Embodiments

In some embodiments, the present teachings relate to the production of enzymes, for example phytase, with increased stability due to increased glycosylation. In some embodiments, the present teachings relate to the modification or alteration of enzymes, for example phytases, to introduce or increase the number of glycosylation sites. In some embodiments this involves introducing into the polypeptide an amino acid motif known to be recognised as an N-linked glycosylation site.

In a further embodiment, the present teachings also relate to increasing the glycosylation of an enzyme through production methods. In some embodiments the production method used is expression in filamentous fungi host, for example a Trichoderma species fungi such as T. reesei.

The present teachings also relate to expression of an enzyme, such as phytase, in an altered host, wherein alteration deletes the function of one of more genes, and in some embodiments deletes the function of the endo glucosaminidase gene.

The present teachings further relate to the production of food and/or feed comprising the modified enzymes of the present teachings. In some embodiments the food or feed product is in the form of pellets.

The present teachings also provide a method of preparing a food or a feed ingredient or supplement, the method comprising admixing or adding the phytases produced by the process of the present teachings, or a composition comprising the phytases according to the present teachings, with another food ingredient. The method for preparing a food or a food ingredient is also another embodiment of the present teachings. Such methods may involve pelleting. To prepare a food or feed ingredient, the enzymes of the present teachings can be added in the form of a solid, a formulation such as a pre-mix, or a liquid. A solid form is typically added before or during the mixing step; and a liquid form is typically added after the pelleting step.

Some embodiments of the present teachings are phytase enzymes with improved is pelleting performance due to glycosylation. In particular, the present teachings relate to thermostable phytases which retain their activity after pelleting and thus increase the levels of available phosphates in animal feed. In some embodiments, the stability arises from inactivity reversibility. In some embodiments, the stability arises from improved recovered activity following treatment such as heat.

In one embodiment, the active enzyme to be produced or modified is BP17. BP17 is an enzyme variant of a Buttiauxella sp. phytase. The sequence for BP17 (excluding signal peptide), which is used as a reference for position numbering of amino acids throughout, is as follows:

SEQ ID NO: 1
NDTPASGYQVEKVVILSRHGVRAPTKMTQTMRDVTPNTWPEWPVKLGYIT

PRGEHLISLMGGFYRQKFQQQGILSQGSCPTPNSI

YVWTDVAQRTLKTGEAFLAGLAPQCGLTIHHQQNLEKADPLFHPVKAGIC

SMDKTQVQQAVEKEAQTPIDNLNQHYIPSLALMNT

TLNFSKSPWCQKHSADKSCDLGLSMPSKLSIKDNGNEVSLDGAIGLSSTL

AEIFLLEYAQGMPQAAWGNIHSEQEWALLLKLHNV

YFDLMERTPYIARHKGTPLLQAISNALNPNATESKLPDISPDNKILFIAG

HDTNIANIAGMLNMRWTLPGQPDNTPPGGALVFER

LADKSGKQYVSVSMVYQTLEQLRSQTPLSLNQPAGSVQLKIPGCNDQTAE

GYCPLSTFTRVVSQSVEPGCQLQ

In another embodiment, the active enzyme to be is produced or modified BP11. BP11 is an enzyme variant of a Buttiauxella sp. phytase. The sequence for BP11 (excluding signal peptide) is as follows:

SEQ ID NO: 2
NDTPASGYQVEKVVILSRHGVRAPTKMTQTMRDVTPNTWPEWPVKLGYIT

PRGEHLISLMGGFYRQKFQQQGILSQGSCPTPNSI

YVWTDVDQRTLKTGEAFLAGLAPQCGLTIHHQQNLEKADPLFHPVKAGIC

SMDKTQVQQAVEKEAQTPIDNLNQHYIPSLALMNT

TLNFSKSPWCQKHSADKSCDLGLSMPSKLSIKDNGNEVSLDGAIGLSSTL

AEIFLLEYAQGMPQAAWGNIHSEQEWALLLKLHNV

YFDLMERTPYIARHKGTPLLQAISNALNPNATESKLPDISPDNKILFIAG

HDTNIANIAGMLNMRWTLPGQPDNTPPGGALVFER

LADKSGKQYVSVSMVYQTLEQLRSQTPLSLNQPAGSVQLKIPGCNDQTAE

GYCPLSTFTRVVSQSVEPGCQLQ

In another embodiment, the active enzyme to be produced or modified is BP111. BP111 is an enzyme variant of a Buttiauxella sp. phytase. The sequence for BP111 (excluding signal peptide) is as follows:

SEQ ID NO: 3
NDTPASGYOVEKVVILSRHGVRAPTKMTQTMRDVTPYTWPEWPVKLGYIT

PRGEHLISLMGGFYROKFQQQGILPRGSCPTPNSI

YVWTDVAQRTLKTGEAFLAGLAPQCGLTIHHQQNLEKADPLFHPVKAGIC

SMDKTQVQQAVEKEAQTPIDNLNQRYIPELALMNT

ILNFSKSPWCQKHSADKPCDLALSMPSKLSIKDNGNEVSLDGAIGLSSTL

AEIFLLEYAQGMPQVAWGNIHSEQEWALLLKLHNV

YFDLMERTPYIARHKGTPLLQAISNALNPNATESKLPDISPDNKILFIAG

HDTNIANIAGMLNMRWTLPGQPDNTPPGGALVFER

LADKSGKQYVSVSMVYQTLEQLRSQTPLSLNQPPGSVOLKIPGCNDQTAE

GYCPLSTFTRVVSQSVEPGCQLQ

All of these phytases are variants of the wild-type sequence such as that derived from Buttiauxella sp. strain P 1-29 deposited under accession number NCIMB 41248, having the sequence as follows:

SEQ ID NO: 4
NDTPASGYQVEKVVILSRHGVRAPTKMTQTMRDVTPNTWPEWPVKLGYIT

PRGEHLISLMGGFYRQKFQQQGILSQGSCPTPNSI

YVWADVDQRTLKTGEAFLAGLAPQCGLTIHHQQNLEKADPLFHPVKAGTC

SMDKTQVQQAVEKEAQTPIDNLNQHYIPFLALMNT

TLNFSTSAWCQKHSADKSCDLGLSMPSKLSIKDNGNKVALDGAIGLSSTL

AEIFLLEYAQGMPQAAWGNIHSEQEWASLLKLHNV

QFDLMARTPYIARHNGTPLLQAISNALNPNATESKLPDISPDNKILFIAG

HDTNIANIAGMLNMRWTLPGQPDNTPPGGALVFER

LADKSGKQYVSVSMVYQTLEQLRSQTPLSLNQPAGSVQLKIPGCNDQTAE

GYCPLSTFTRVVSQSVEPGCQLQ

The above detailed phytase enzymes are mature proteins lacking a signal sequence. The appropriate signal sequence derived from *Buttiauxella* sp. strain P 1-29 deposited under accession number NCIMB 41248, is as follows:

SEQ ID NO: 12
MTISAFNRKKLTLHPGLFVALSAIFSLGSTAYA

In a further embodiment, the present teachings relate to the alteration or modification of a phytase enzyme to introduce a motif known to be recognised as an N-linked glycosylation site. In some embodiments the motif is Asn-Xaa-Ser/Thr, wherein Asn is asparagine (N), Xaa can be any amino acid, Ser is serine (S) and Thr is threonine (T). Ser and Thr are equal alternatives. Such alteration can be carried out using techniques such as site-directed mutagenesis. Such alteration may involve introducing one or two or all three of the amino acids of the motif Asn-Xaa-Ser/Thr into the polypeptide.

The phytase BP17 amino acid sequence (SEQ ID NO:1) contains three potential N-linked glycosylation sites according to analysis by the NetNGlyc 1.0 prediction algorithm (http://www.cbs.dtu.fk/services/NetNGlyc/). The asparagine residues that are predicted to be glycosylated are residues N169, N173 and N285 of the mature phytase BP17 sequence, SEQ ID NO:1.

In one embodiment of the present teachings involves the production and use of a phytase which is highly glycosylated, for example highly glycosylated BP17, or a homologue, variant or derivative thereof. In some embodiments, the enzyme produced and/or used has more than 75%, for example more than 80%, for example more than 90% and for further example more than 95%, 96%, 97%, 98%, 99%, or 99.9% identity to BP17.

Some embodiments of the present teachings involve introducing further glycosylation sites to BP17. Specifically one or more or all of the following substitutions can be introduced to BP17 (with reference to the position numbering of SEQ ID NO:1, lacking a signal sequence) in order to introduce glycosylation sites: E121T, P394N, D386N, K202N and N204T, Q151N and P153S, P373T, and Q76N.

In particular, a sequence of the present teachings may comprise K202N and N204T in the same sequence. In a further embodiment of the present teachings, a sequence of the present teachings may comprise Q151N and P153S in the same sequence. In a further embodiment of the present teachings, a sequence of the present teachings may comprise D386N.

The following may comprise sequences of the present teachings (in each case the amino acid changes relative to BP17 are shown in bold and underlined) wherein amino acid substitutions have been introduced to BP17 (SEQ ID NO:1) to increase the number of glycosylation sites:

SEQ ID NO: 5
(E121T)
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLTKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ

SEQ ID NO: 6
(P394N)
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCNLSTFTR

VVSQSVEPGCQLQ

SEQ ID NO: 7
(D386N)
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNNQTAEGYCPLSTFTR

VVSQSVEPGCQLQ

SEQ ID NO: 8
(K202N and N204T)
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

INDTGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ

SEQ ID NO: 9
(Q151N and P153S)
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA

NTSIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ

SEQ ID NO: 10
(P373T)
NDTPASGYQVEKVVILSRHGVRAPTKMTQTMRDVTPNTWPEWPVKLGYIT

PRGEHLISLMGGFYRQKFQQQGILSQGSCPTPNSIYVWTDVAQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQTAGSVQLKIPGCNDQTAEGYCPLSTFTR

VVSQSVEPGCQLQ

SEQ ID NO: 11
(Q76N)
NDTPASGYQVEKVVILSRHGVRAPTKMTQTMRDVTPNTWPEWPVKLGYIT

PRGEHLISLMGGFYRQKFQQQGILSNGSCPTPNSIYVWTDVAQRTLKTGE

AFLAGLAPQCGLTIHHQQNLEKADPLFHPVKAGICSMDKTQVQQAVEKEA

QTPIDNLNQHYIPSLALMNTTLNFSKSPWCQKHSADKSCDLGLSMPSKLS

IKDNGNEVSLDGAIGLSSTLAEIFLLEYAQGMPQAAWGNIHSEQEWALLL

KLHNVYFDLMERTPYIARHKGTPLLQAISNALNPNATESKLPDISPDNKI

LFIAGHDTNIANIAGMLNMRWTLPGQPDNTPPGGALVFERLADKSGKQYV

SVSMVYQTLEQLRSQTPLSLNQPAGSVQLKIPGCNDQTAEGYCPLSTFTR

VVSQSVEPGCQLQ

The extent of glycosylation of an enzyme may increase the reversibility of heat inactivation of the modified enzyme compared to the wild-type enzymes or the enzyme parent from which the enzyme is derived.

Some embodiments of the present teachings provide phytase enzymes with increased inactivity reversibility. In some embodiments such enzymes are BP17, glycosylated. In some embodiments, the present teachings provide enzymes comprising SEQ ID NOs: 5, 6, 7, 8, 9, 10 and 11, or homologues, variants or derivative thereof, which have increased inactivity reversibility. In some embodiments such enzymes have more than 10%, 20%, 30%, 40%, 50%, 60%, 70%, 80%, 90%, 100%, 110%, 120%, 140%, 160%, 180%, or 200% increased inactivity reversibility compared to a control phytase.

The present teachings also provide for nucleic acids encoding and capable of encoding the polypeptides of SEQ ID NOs:5, 6, 7, 8, 9, 10 and 11, or homologues, variants or derivative thereof.

The present teachings can also relate to an enzyme of any of SEQ ID NOs:1-11 or a polypeptide derived from this (parent) enzyme by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein. In some embodiments such enzymes have more than 75%, for example more than 80%, for example more than 90%, and for further example more than 95%, 96%, 97%, 98%, or 99% identity to SEQ ID NOs:1-11. In some embodiments this enzyme is glycosylated and in some embodiments such an enzyme has increased inactivity reversibility and/or increased recovered activity following a treatment such as heat.

A further embodiment of the present teachings provides a method of producing an enzyme, for example an enzyme wherein glycosylation is increased or the enzyme is highly glycosylated. This method involves altering the amino acid sequence of the enzyme, or altering the nucleic acid which encodes the enzyme, to increase the number of glycosylation sites. In some embodiments this alteration involves increasing the number of N-linked glycosylation sites. In some embodiments this involves introducing the motif is Asn-Xaa-Ser/Thr to the enzyme or introducing sequence which encodes this site to the nucleic acid. In some embodiments one, or two or three or more glycosylation sites are introduced to an enzyme.

In some embodiments the enzymes of the present teachings are used in food or feed, in the preparation of food or feed and/or in food or feed additives or their preparation. In some embodiments the enzymes may form a composition with other food or feed ingredients, or may be added to a composition of food or feed ingredients. In some embodiments the enzymes have more inactivity reversibility, and/or improved recovered activity following a treatment such as heat, as comparative or similar enzymes used in food or feed production.

Phytase enzymes, such as BP17 (SEQ ID NO:1) are historically added to animal feed to increase phosphate availability thus increasing the nutritional value of the product. The processing of the feed, for example under heat and high pressure, can denature the phytase and reduce its activity. The present teachings provide a more thermostable phytase which therefore increases the post-processing levels of phytase activity present in the feed. In some embodiments the feed processing involves the formation of pellets. In further embodiments the pellets comprising the phytase have increased post-processing levels of phytase activity.

Production Methods

In further embodiments, the present teachings also relate to increasing the glycosylation of an enzyme through production methods. In some embodiments the production method used is expression in a filamentous fungi host, for example expression in *Trichoderma* species fungi and specifically for example in *T. reesei*.

The present teachings also relate to expression of an enzyme in an altered host, wherein alteration has deleted the function of one of more genes, and in some embodiments has deleted the function of the endo glucosaminidase gene.

In one embodiment, the present teachings provide for the expression and production of a phytase enzyme, and in some embodiments the phytase is BP17, which may or may not be modified, in *Trichoderma* species fungi, for example in *T. reesei*, wherein the endo glucosaminidase gene has been deleted.

In some embodiments, the present teachings relate to the production of enzymes, such as phytase, with increased glycosylation. In further embodiments increased glycosylation is encouraged by the use of a host with a deleted endo glucosaminidase gene. In some embodiments the enzyme produced has increased inactivity reversibility compared to an enzyme produced using different methods, especially methods using a different host species and/or a host wherein the endo glucosaminidase gene is not deleted. In some embodiments the enzyme produced has increased stability compared to an enzyme produced using different methods, especially methods using a different host species and/or a host wherein the endo glucosaminidase gene is not deleted.

The extent of glycosylation of a protein, such as an enzyme, is greater if it is produced in a host deleted of the endogenous endo glucosaminidase. According to some embodiments of the present teachings the endo glucosaminidase gene may be deleted by removal, disruption, interference or any method which prevents or reduced the expression and production of endo glucosaminidase in the host.

In some embodiments the present teachings relate to the expression and production of a phytase in an endo glucosaminidase deleted host. In further embodiments the phytase is BP17 or a homologue, variant or derivative thereof, for example having more than 75%, for example more than 80%, for example more than 90%, and for further example more than 95%, 96%, 97%, 98%, or 99% identity to BP17 (SEQ ID NO:1) or any of SEQ ID NOs:2-11. In some embodiments the host is a filamentous fungi host, for example a *Trichoderma* species fungi and for further example *T. reesei*. In some embodiments the phytase has increased inactivity reversibility compared to a phytase produced by other production methods, or a phytase which is not glycosylated or not highly glycosylated.

In some embodiments the enzymes produced by the methods of the present teachings are used in food or feed, in the preparation of food or feed and/or in food or feed additives or their preparation. In some embodiments the enzymes of the current teachings may form a composition with other food or feed ingredients, or may be added to a composition of food or feed ingredients. In some further embodiments the enzymes of the present teachings have a higher inactivity reversibility of than other enzymes used in food or feed production.

In some embodiments, the production methods of the present teachings provide a phytase having an increased inactivity reversibility, which therefore increases the post-processing levels of phytase activity present in feed. In some embodiments the feed processing involves the formation of pellets. In further embodiments the pellets comprising the phytase of the current teachings have increased post-processing levels of phytase activity. In yet further embodiments the phytase of the current teachings is better able to survive the pelleting process and retain post-processing levels of phytase activity.

Granule and Multi-layered Granule

Cores, granules and multi-layered granules may be produced by a variety of fabrication techniques including: rotary atomization, wet granulation, dry granulation, spray drying, disc granulation, extrusion, pan coating, spheronization, drum granulation, fluid-bed agglomeration, high-shear granulation, fluid-bed spray coating, crystallization, precipitation, emulsion gelation, spinning disc atomization and other casting approaches, and prill processes. Such processes are known in the art and are described in U.S. Pat. No. 4,689,297 and U.S. Pat. No. 5,324,649 (fluid bed processing); EP656058B1 and U.S. Pat. No. 454332 (extrusion process); U.S. Pat. No. 6,248,706 (granulation, high-shear); and EP804532B1 and U.S. Pat. No. 6,534,466 (combination processes utilizing a fluid bed core and mixer coating).

The core is the inner nucleus of the multi-layered granule or is the granule. The materials used in the core can be suitable for the use in foods and/or animal feeds. US20100124586, WO9932595, and U.S. Pat. No. 5,324,649 detail suitable materials for the core.

In one embodiment, the core comprises one or more water soluble or dispersible agent(s). Suitable water soluble agents include, but are not limited to, inorganic salts (e.g. sodium sulphate, sodium chloride, magnesium sulphate, zinc sulphate, and ammonium sulphate), citric acid, sugars (e.g. sucrose, lactose, glucose, granulated sucrose, maltodextrin and fructose), plasticizers (e.g. polyols, urea, dibutyl phthalate, and dimethyl phthalate), fibrous material (e.g. cellulose and cellulose derivatives such as hydroxyl-propyl-methyl cellulose, carboxy-methyl cellulose, and hydroxyl-ethyl cellulose), phytic acid, and combinations thereof. Suitable dispersible agents include, but are not limited to, clays, nonpareils (combinations of sugar and starch; e.g. starch-sucrose non-pareils—ASNP), talc, silicates, carboxymethyl cellulose, starch, and combinations thereof.

In one embodiment, the core comprises sodium sulphate. In another embodiment, the core consists of sodium sulphate. In some embodiments, the core may comprise a phytase and/or phytic acid. In some embodiments, the core does not comprise phytase.

In some embodiments the core is coated with at least one coating layer. In one embodiment the core is coated with at least two coating layers. In another embodiment the core is coated with at least three coating layers. In a further embodiment the core is coated with at least four coating layers.

The materials used in the coating layer(s) can be suitable for use in foods and/or animal feeds. US20100124586, WO9932595, and U.S. Pat. No. 5,324,649 detail suitable materials for the coating layer.

In some embodiments, the fluid bed granulation process is employed traditionally by running and by continuously spraying one layer on top of the next layer with only a brief flushing of the lines and spray nozzles with water for cleaning purposes, without cessation in spray. In some embodiments, the granules can be made by allowing them to dry (fluidize without spray) for an additional time period (eg 5 minutes) after the end of each intermediate spray (for example at 70 C), and an optional additional drying after the final spray can be performed (for example 20 minutes at 70 C).

In some embodiments, the additional time period after the end of the intermediate spray is at least 1, 2, 3, 4, 5, 6, 7, 8, 9, 10, 11, 12, 15, 20, or 25 minutes. In some embodiments the additional time period after the end of the intermediate spray is 2-8, 3-7, or 4-6 minutes. In some embodiments, the temperature of the additional time period after the end of the intermediate spray is at least 50 C, 55 C, 60 C, 65 C, 70 C, 75 C, or 80 C. In some embodiments, the temperature of the additional time period after the end of the intermediate step is 60 C-80 C or 65 C-75 C. In some embodiments, after the end of the intermediate spray a drying step is performed for 4-6 minutes at 65-75 C.

In some embodiments, the optional drying after the final spray can be at least 5, 10, 15, 20, 25, or 30 minutes. In some embodiments, the optional drying after the final spray can be 5-30 or 10-25 minutes. In some embodiments, the temperature of the optional drying after the final spray is at least 50 C, 55 C, 60 C, 65 C, 70 C, 75 C, or 80 C. In some embodiments, the temperature of the optional drying after the final spray is 60 C-80 C or 65 C-75 C. In some embodiments, the optional drying after the final spray is 15-25 minutes at 65 C-75 C.

In one embodiment, a coating layer comprises one of more of the following materials: an inorganic salt (e.g. sodium sulphate, sodium chloride, magnesium sulphate, zinc sulphate, and ammonium sulphate), citric acid, a sugar (e.g. sucrose, lactose, glucose, and fructose), a plasticizer (e.g. polyols, urea, dibutyl phthalate, and dimethyl phthalate), fibrous material (e.g. cellulose and cellulose derivatives such as hydroxyl-propyl-methyl cellulose, carboxymethyl cellulose, and hydroxyl-ethyl cellulose), clay, nonpareil (a combination of sugar and starch), silicate, carboxymethyl cellulose, phytic acid, starch (e.g. corn starch), fats, oils (e.g. rapeseed oil, and paraffin oil), lipids, vinyl polymers, vinyl copolymers, polyvinyl alcohol (PVA), plasticizers (e.g. polyols, urea, dibutyl phthalate, dimethyl phthalate, and water), anti-agglomeration agents (e.g. talc, clays, amorphous silica, and titanium dioxide), anti-foam agents (such as Foamblast 882® and Erol 6000K®), and talc. US20100124586, WO9932595, and U.S. Pat. No. 5,324,649 detail suitable components for the coating layers.

In one embodiment, the coating layer comprises sugars, such as sucrose.

In one embodiment, the coating layer comprises a polymer such as polyvinyl alcohol (PVA).

Suitable PVA for incorporation in the coating layer(s) of the multi-layered granule include partially hydrolyzed, fully hydrolyzed and intermediately hydrolyzed having low to high degrees of viscosity.

In another embodiment, the coating layer comprises an inorganic salt, such as sodium sulphate.

In one embodiment, at least one coating layer is an enzyme coating layer. In some embodiments the core is coated with at least two enzyme layers. In another embodiment the core is coated with at least three enzyme layers.

In some embodiments, the granules of the present teachings comprise an enzyme coating layer. In some embodiments, the enzyme layer comprises at least one enzyme. In some embodiments the enzyme layer comprises at least two enzymes. In some embodiments, the enzyme layer comprises at least three enzymes. In some embodiments, the enzyme is selected from the group consisting of phytases, xylanases, phosphatases, amylases, esterases, redox enzymes, lipases, transferases, cellulases, hemi-cellulases, beta-glucanases, oxidases (e.g. hexose oxidases and maltose oxidoreductases), proteases and mixtures thereof. Generally, at least one enzyme coating layer comprises at least one phytase, and phytic acid.

In one embodiment, the enzyme coating layer comprises at least one phytase and at least one further enzyme selected from the group consisting of phytases, xylanases, phosphatases, amylases, esterases, redox enzymes, lipases, transferases, cellulases, hemi-cellulases, beta-glucanases, oxidases (e.g. hexose oxidases and maltose oxidoreductases), and proteases.

The above enzyme lists are examples only and are not meant to be exclusive. Any enzyme can be used in the granules described herein, including wild type, recombinant and variant enzymes of bacterial, fungal, yeast, plant, insect and animal sources, and acid, neutral or alkaline enzymes.

In some embodiments, the enzyme coating layer may further comprise one or more additional materials selected from the group consisting of: phytic acid, sugars (e.g. sucrose), starch (e.g. corn starch), fats, oils (e.g. rapeseed oil, and paraffin oil), lipids, vinyl polymers, vinyl copolymers, polyvinyl alcohol (PVA), plasticizers (e.g. polyols, urea, dibutyl phthalate, dimethyl phthalate, and water), anti-agglomeration agents (e.g. talc, clays, amorphous silica, and titanium dioxide), anti-foam agents (such as Foamblast 882® and Erol 6000K® available from Ouvrie PMC, Lesquin, France), and talc. US20100124586, WO9932595, and U.S. Pat. No. 5,324,649 detail suitable components for granules. Foamblast 882® is available from Emerald Foam Control, LLC. Foamblast 882® is a defoamer which is made with food grade ingredients.

In one embodiment, the enzyme coating layer comprises phytic acid and at least one phytase. In other words, the phytase and phytic acid are incorporated into the same layer of a multi-layered granule.

In one embodiment, the multi-layered granule comprises an enzyme coating layer comprising a phytase and a coating layer comprising phytic acid that is functionally adjacent to the enzyme layer.

In one embodiment, the coating layer comprises phytic acid wherein said coating layer is functionally adjacent to a core comprising phytase and/or an enzyme coating layer comprising phytase.

In one embodiment, the outer coating layer of a multi-layered granule comprises one or more of the following coating materials: polymers (e.g. vinyl polymers, polyvinyl alcohol, and vinyl copolymers), gums, waxes, fats, oils, lipids, lecithin, pigments, lubricants, nonpareils, inorganic salts (e.g. sodium sulphate, sodium chloride, magnesium sulphate, zinc sulphate, and ammonium sulphate), talc, and plasticizers (e.g. sugars, sugar alcohols, and polyethylene glycol).

In one embodiment, the outer coating layer of a multi-layered granule comprises an inorganic salt (e.g. sodium sulphate), polyvinyl alcohol (PVA), talc or combinations thereof. In one embodiment, the outer coating layer comprises polyvinyl alcohol (PVA) and/or talc.

In one embodiment, the outer coating layer prevents or reduces the rate or extent of water, moisture or steam migration into the enzyme layer.

The multi-layered granules described herein can be produced by a variety of techniques including: fluid-bed spray-coating, pan-coating, and other techniques for building up a multi-layered granule by adding consecutive layers on top of the starting core material (the seed). See, for example, U.S. Pat. No. 5,324,649 and US20100124586. In one embodiment, the multi-layered granules are produced using a fluid-bed spray coating process.

In one embodiment, the multi-layered granules comprise or consist of a core comprising sodium sulphate; a first coating layer comprising or consisting of phytase, sucrose, starch, phytic acid and rapeseed oil; a second coating layer comprising or consisting of sodium sulphate; and a third coating layer comprising or consisting of talc and PVA. The first coating layer is applied to the core then the second coating layer is applied to the first coating layer and then the third coating layer is applied to second coating layer.

In another embodiment, the multi-layered granules comprise or consist of a core comprising sodium sulphate; a first coating layer comprising or consisting of phytase, sucrose, starch, phytic acid and an antifoam agent (such as Foamblast 882®); a second coating layer comprising or consisting of sodium sulphate; and a third coating layer comprising or consisting of talc and PVA. The first coating layer is applied to the core then the second coating layer is applied to the first coating layer and then the third coating layer is applied to second coating layer.

Combinations of Embodiments

In a further embodiment, facets of the present teachings can be combined. In other words, a phytase enzyme of the present teachings which has been modified to increase the number of glycosylation sites by altering the amino acid sequence, can be produced in an altered host, for example a host wherein the endo glucosaminidase gene has been deleted. This can maximise the extent of glycosylation of the enzyme. In some embodiments the host is a *Trichoderma* species fungi, for example *T. reesei*.

In some embodiments, the enzyme expressed in the altered host is a phytase, for example BP17 (SEQ ID NO:1) or wild-type phytase such as SEQ ID NO:4, or a modified phytase of any one of SEQ ID NOs:2, 3, 5-11 or a homologue, variant or derivative thereof, for example having more than 75%, for example more than 80%, for example more than 90%, and for further example more than 95%, 96%, 97%, 98%, or 99% identity to BP17 (SEQ ID NO:1) or any of SEQ ID NOs:2-11.

In particular, the improvements in enzyme characteristics typified by the enzymes of the present teachings and/or produced by the methods of the present teachings, can be directed to enzyme stability under food and feed processing conditions, to the enzyme stability during stomach transit, and to the enzyme activity and stability in human or animal stomach and/or intestinal tract, making the improved variants particularly suitable for use as feed supplements. Thus, such improvements comprise the increased inactivity reversibility and/or recovered activity arising after exposure to elevated temperatures, in some embodiments at temperatures above 65 C, above 75 C, above 85 C and in further embodiments above 95 C. Additionally, other parameters impacted can include the increase in stability against proteolytic digestion, for example protease of the digestive tract such as pepsin, the increase in catalytic activity at low pH, for example catalytic activity below pH 5.5, and the general efficiency of releasing phosphate groups from phytate, and in some examples in addition inositol phosphates.

In another embodiment of the present teachings there is provided a method for the production of food or animal feed. Animal feed is typically produced in feed mills in which raw materials are first ground to a suitable particle size and then mixed with appropriate additives. The enzymes of present teachings, or enzymes produced by the methods of the present teachings, may be added to feed ingredients. The feed may then be produced as a mash or pellets; the later typically involves a method by which the temperature is raised to a target level and then the feed is passed through a die to produce pellets of a particular size. Subsequently liquid additives such as fat and enzyme may be added. The pellets are allowed to cool prior to transportation. Production of animal feed may also involve an additional step that includes extrusion.

A further embodiment the present teachings provide methods for the preparation of an animal feed comprising a phytase enzyme variant, said method comprising the sequential steps of i) performing one or more of the above methods of preparing a phytase enzyme variant, and ii) adding the prepared phytase enzyme variant to an animal feed. In some embodiments, the feed composition comprises a phytase at a concentration of 10-10000 Ukg feed, 200-2000Ukg feed, or 500-1000 U/kg feed.

EXAMPLES

The following examples are intended to illustrate some embodiments of the present teachings.

Example 1

Expression of *Buttiauxella* Phytase BP-17 in *T. reesei* Host Cells

Construction of a Phytase BP-17 Expression Vector.

The open reading frame of BP-17 variant of *Buttiauxella* phytase (US2009098249A1) was amplified by polymerase chain reaction (PCR) using DNA synthesized by GeneArt AG (Regensburg, Germany) as the template (SEQ ID NO:13).

```
                                          (SEQ ID NO: 13)
ACTAGTGTCGCCGTGGAGAAGCGCAACGACACCCCCGCCAGCGGCTACCA

GGTCGAGAAGGTCGTCATCCTCAGCCGCCACGGCGTCCGCGCCCCTACCA

AGATGACCCAGACCATGCGCGACGTCACCCCCAACACCTGGCCCGAGTGG

CCCGTCAAGCTCGGCTACATCACCCCTCGCGGCGAGCACCTCATCAGCCT

CATGGGCGGCTTCTACCGCCAGAAGTTCCAGCAGCAGGGCATCCTCAGCC

AGGGCTCGTGCCCCACCCCCAACAGCATCTACGTCTGGACCGACGTCGCC

CAGCGCACCCTCAAGACCGGCGAGGCCTTCCTCGCCGGCCTCGCCCCCCA

GTGCGGCCTCACCATCCACCACCAGCAGAACCTCGAGAAGGCCGACCCCC

TCTTCCACCCCGTCAAGGCCGGCATCTGCAGCATGGACAAGACCCAGGTC

CAGCAGGCCGTCGAGAAGGAGGCCCAGACCCCCATCGACAACCTCAACCA

GCACTACATCCCCAGCCTCGCCCTCATGAACACCACCCTCAACTTCAGCA

AGAGCCCCTGGTGCCAGAAGCACAGCGCCGACAAGAGCTGCGACCTCGGC

CTCAGCATGCCCAGCAAGCTCAGCATCAAGGACAACGGCAACGAGGTCTC

CCTCGACGGCGCTATCGGCCTCAGCTCCACCCTCGCCGAGATCTTCCTCC

TCGAGTACGCCCAGGGCATGCCTCAGGCCGCCTGGGGCAACATCCACAGC

GAGCAGGAGTGGGCCCTCCTCCTCAAGCTCCACAACGTCTACTTCGACCT

CATGGAGCGCACCCCCTACATCGCCCGCCACAAGGGCACCCCCCTCCTCC

AGGCCATCAGCAACGCCCTCAACCCCAACGCCACCGAGAGCAAGCTCCCC

GACATCAGCCCCGACAACAAGATCCTCTTCATCGCCGGCCACGACACCAA

CATCGCCAACATCGCCGGCATGCTCAACATGCGCTGGACCCTCCCCGGCC

AGCCCGACAACACCCCCCCTGGCGGCGCTCTCGTCTTTGAGCGCCTCGCC

GACAAGTCCGGCAAGCAGTACGTCAGCGTCAGCATGGTCTACCAGACCCT

CGAGCAGCTCCGCAGCCAGACCCCCCTCAGCCTCAACCAGCCTGCCGGCA

GCGTCCAGCTCAAGATCCCCGGCTGCAACGACCAGACCGCCGAGGGCTAC

TGCCCCCTCAGCACCTTCACCCGCGTCGTCAGCCAGAGCGTCGAGCCCGG

CTGCCAGCTCCAGTAAGGCGCGCC.
```

The PCR machine used was a Peltier Thermal Cycler PTC-200 (MJ Research). The DNA polymerase used in the PCR was Herculase (Stratagene). The primers used to amplify the phytase open reading frame were primer SK680 (forward) 5'-CACCATGCAGACCTTCGGT-GCTTTTCTCGTTTCCTTCCTCGCCGCC AGCGGC- CTGGCCGCGGCCAACGACACCCCCGCCAGC-3' (SEQ ID NO:14), and primer SK6 5'-CCTTACTG-GAGCTGGCAG-3'(SEQ ID NO:15).

The forward primer contained an additional four nucleotides (sequence—CACC) at the 5' end that was required for cloning into the pENTRY/D-TOPO vector (Invitrogen) and a sequence encoding a native *T. reesei* signal sequence to direct secretion of phytase BP-17.

The PCR conditions for amplifying the *Buttiauxella* phytase open reading frame were as follows: Step 1: 94 C for 1 min. Step 2: 94 C for 30 sec. Step 3: 58 C for 30 sec. Step 4: 72 C for 5 min. Repeat steps 2-4 for 30 cycles. Step 5: 4 C for storage. The PCR product was purified using Qiaquick Gel Purification Kit (Qiagen). The purified PCR product was initially cloned into the pENTRY/D TOPO vector (Invitrogen), and transformed into TOP 10 chemically competent *E. coli* cells (Invitrogen). A pENTR/D-TOPO vector with the correct sequence of the phytase open reading frame was recombined with the pTrex3g vector using LR clonase II (Invitrogen) according to the manufacturer's instructions to create pTrex3g/BP-17 (see FIG. 1).

Plasmid pTrex3g/BP-17 was used as template for preparative PCR with primers SK745 5'-GAGTTGT-GAAGTCGGTAATCC (SEQ ID NO:16) and SK746 5'-CTGGAAACGCAACCCTGAAG (SEQ ID NO:17) and the approximately 5.8 kb DNA fragment (the phytase BP-17 expression cassette) was purified using the Qiagen PCR purification kit.

In more detail, this PCR product contains the following segments of DNA
1. The *T. reesei* cbh1 promoter region. This promoter sequence begins at a position approximately 1500 bp upstream of the cbh1 start codon and ends 16 bp upstream of the cbh1 start codon.
2. The sequence atcacaagtttgtacaaaaaagcaggctccgcggc-cgcccccttcacc (SEQ ID NO:18) is in between the cbh1 promoter and the signal sequence/BP-17 coding sequence. The section of this sequence shown in bold is the phage lambda attB1 recombination site of 25 bp (attB1).
3. The synthetic coding region encoding for the mature *Buttiauxella* phytase variant (1242 bp), directly fused to the end of the signal sequence (60 bp).
4. The sequence ggaacggtggccgcgcgccgacccagctttcttgta-caaagtggtgatcgcgcc (SEQ ID NO:19) is in between the 3' end of the BP-17 coding sequence and the cbh1 terminator region. The section of this sequence shown in bold is the phage lambda attB recombination site of 25 bp (attB2).
5. The native *T. reesei* cbh1 terminator region (356 bp) immediately follows the coding region of the phytase.
6. A 2.75 kb fragment of *Aspergillus nidulans* genomic DNA including the promoter, coding region and terminator of the amdS (acetamidase) gene. This fragment begins at a naturally occurring SspI site and ends immediately prior to a naturally occurring XbaI site.

Transformation of a Strain of *T. reesei* with Phytase BP-17 Expression Cassette A quad deleted strain of *T. reesei* (Δcbh1, Δcbh2, Δegl1, Δegl2) is described in WO05/001036. This strain was transformed with the phytase BP-17 expression cassette using the transformation method described by Penttilä et al. (Penttilä M., Nevalainen, H., Ratto, M., Salminen, E. and Knowles, J. 1987. A versatile transformation system for the cellulolytic filamentous fungus *Trichoderma reesei*. Gene 61: 155-164).

The transformants were selected on a selective medium containing acetamide as a sole source of nitrogen (sorbitol 218 g/l; acetamide 0.6 g/l; cesium chloride 1.68 g/l; glucose 20 g/l; potassium dihydrogen phosphate 15 g/l; magnesium sulfate heptahydrate 0.6 g/l; calcium chloride dehydrate 0.6 g/l; iron (II) sulfate 5 mg/l; zinc sulfate 1.4 mg/l; cobalt (II) chloride 1 mg/l; manganese (II) sulfate 1.6 mg/l; agar 20 g/l; pH 4.25). Transformed colonies appeared in about 1 week. Individual transformants were transferred onto fresh acetamide selective plates and allowed to grow for 2-4 days.

Isolates exhibiting stable growth on selective medium were used to inoculate 50 ml of lactose defined medium ($(NH_4)_2SO_4$ 5 g/l; PIPPS buffer 33 g/l; Bacto Casamino Acids 9 g/l; $KH_2PO_4$ 4.5 g/l; $CaCl_2*2H_2O$ 1.32 g/l; $MgSO_4*7H_2O$ 1 g/l; Mazu DF204 5 ml/l; 400× Trace Elements 2.5 ml/l; pH 5.5; lactose (sterilized separately) 16 g/l. 400× Trace Elements solution: Citric acid (anhydrous) 175 g/l; $FeSO_4*7H_2O$ 200 g/l; $ZnSO_4*7H_2O$ 16 g/l; $CuSO_4*5H_2O$ 3.2 g/l; $MnSO_4*4H_2O$ 1.4 g/l; $H_3BO_3$ 0.8 g/l.) in 250 ml shake flasks The flasks were shaken for 4-5 days at 28 C.

The culture medium was separated by filtration and analyzed by polyacrylamide gel electrophoresis in the presence of sodium dodecylsulfate (SDS-PAGE). A new protein band was observed with approximately the expected mobility for phytase BP-17 based on the amino acid sequence. A transformant that produced a high amount of phytase was identified. Phytase produced by this transformant in 14 L bioreactors using the methods described in WO2004/035070 was used in subsequent studies.

Example 2

Expression of *Buttiauxella* Phytase BP-17 in *T. reesei* Host Cells with a Deletion of the Endo Glucosaminidase Gene Construction of a Disruption Cassette for the Endo Glucosaminidase Gene of *T. reesei*.

The *Trichoderma reesei* endo glucosaminidase gene encodes a secreted enzyme that cleaves N-linked glycans from glycoproteins. It was identified in the genomic sequence of *T. reesei* (http://genome.jgi-psf.org/Trire2/Trire2.home.html) using information provided in WO 2006/050584. Its 5' flanking region (1.9 Kb) was amplified by PCR using primers SK915 (5'-CTGATATCCTGGCATGGT-GAATCTCCGTG-3') (SEQ ID NO:20) and SK916 (5'-CATGGCGCGCCGAGGCAGATAGGCGGACGAAG-3') (SEQ ID NO:21). The 3' flanking region (1.7 Kb) was amplified by PCR using primers SK917 (5'-CATG-GCGCGCCGTGTAAGTGCGTGGCTGCAG-3') (SEQ ID NO:22) and SK918 (5'-CTGATATCGATCGAGTCGAACT-GTCGCTTC-3') (SEQ ID NO:23). PfuII Ultra (Stratagene) was used as the polymerase in all PCR reactions.

The products of the PCR reaction were purified with the QIAquick PCR purification kit (Qiagen) by following the protocol listed in the manual. Both amplified DNA fragments were digested with restriction endonuclease AscI, followed by purification of digested DNA using QIAquick kit. The two DNA fragments were mixed and used as a template for a fusion PCR reaction with primers SK915 and SK918. The product of this reaction, a 3.6 kb DNA fragment, was cloned into pCR-Blunt II TOPO vector using the Zero Blunt TOPO PCR Cloning Kit (Invitrogen). The structure of the resulting plasmid (pCR-BluntII-TOPO(5'-3' flank)) was confirmed by restriction analysis.

A mutant form of the *T. reesei* acetolactate synthase (ALS) gene conferring resistance to chlorimuron ethyl (WO 2008/039370) was amplified using PCR primers SK949 (5'-GTTTCGCATGGCGCGCCTGAGACAATGG-3') (SEQ ID NO:24) and SK946 (5'-CACAGGCGCGC-CGATCGCCATCCCGTCGCGTC-3') (SEQ ID NO:25) and pTrex-Glucoamylase vector (WO 2008/039370, Example 2) as the template. The product of the PCR reaction was purified with QIAuick kit, digested with AscI, purified again and ligated with pCR-BluntII-TOPO (5'-3' flank) digested with the same enzyme and purified similarly. The orientation of the insert in the resulting plasmid pCR-BluntII-TOPO(5' flank-ALS marker-3' flank) was established by restriction analysis.

An additional fragment of *T. reesei* chromosomal sequence (referred to as "3'-repeat") was amplified using the same techniques and primers MC40 (5'-CTATGACATGC-CCTGAGGCGATGCTGGCCAGGTACGAGCTG-3') (SEQ ID NO:26) and MC41 (5'-CAGCCTCGCGGTCACA-GTGAGAGGAACGGGGT GAAGTCGTATAAG-3') (SEQ ID NO:27).

This sequence is located on *T. reesei* chromosome further downstream of the 3'-flank area that is contained within pCR-BluntII-TOPO (5'-3' flank). The 0.46 kb product of this PCR (3'-repeat) was cloned upstream of the ALS gene in the pCR-BluntII-TOPO(5' flank-ALS marker-3' flank) using In-Fusion Dry-Down PCR Cloning Kit (Clontech). pCR-BluntII-TOPO(5' flank-ALS marker-3' flank) was digested with Pas I and BstEII for use as a vector to clone in the 3' repeat. The resulting construct pCR-BluntII-TOPO(5' flank-ALS marker-3' repeat-3' flank) was used as the template for a PCR with primers SK1008 (CTAGCGATCGCGTGTG-CACATAGGTGAGTTCTCC) (SEQ ID NO:28) and SK1009:(CTAGCGATCGCGCAGACTGGCATGCCT-CAATC AC) (SEQ ID NO:29).

The 7.5 kb DNA product was cloned into pCR-BluntII-TOPO vector using the corresponding kit from Invitrogen. The resulting plasmid was digested with AsiSI and a 7.5 kb DNA fragment (the endo glucosaminidase deletion cassette) was purified by preparative agarose gel electrophoresis.

Disruption of the Endo Glucosaminidase Gene in *T. reesei*.

A quad deleted strain of *T. reesei* (Δcbh1, Δcbh2, Δegl1, Δegl2) is described in WO05/001036. This strain was transformed with the deletion cassette listed as SEQ ID NO:30 using the transformation method described by Penttilä et al. (Penttilä M., Nevalainen, H., Ratto, M., Salminen, E. and Knowles, J. 1987. A versatile transformation system for the cellulolytic filamentous fungus *Trichoderma reesei*. Gene 61: 155-164). The transformants were selected on a Modified Vogel's medium containing 200 ppm chlorimuron ethyl (WO 2008/039370). Transformants were cultured in liquid medium and culture supernatants were analyzed by SDS gel electrophoresis.

Two clones (#11 and #74) displaying an upward shift in mobility of most of the protein bands on the gel were identified. Chromosomal DNA was isolated from these two strains as well as the parent quad deleted strains of *T. reesei*. PCR analyses were performed on these DNA preparations using primer pairs MC 42 plus MC 48 (5'-CTCGCCATCT-GACAACCTACAAATC-3' (SEQ ID NO:30) and 5'-CTAG-TACCCTGAGTTGTCTCGCCTCC-3') (SEQ ID NO:31) and MC 45 plus MC 50 (5'-CCTCTACCATAACAGGATC-CATCTG-3' (SEQ ID NO:32) and 5'-CGTGAGCTGAT-GAAGGAGAGAACAAAGG-3') (SEQ ID NO:33).

Products of the expected size (2.9 and 2.3 kb) were obtained with DNA isolated from clone #74. This clone was subjected to two successive rounds of purification (by isolation of progeny of a single spore). DNA was isolated from the purified transformant #74. PCR analyses were repeated confirming successful deletion of the endo glucosaminidase gene.

Transformation of the Endo Glucosaminidase Deleted Strain of *T. reesei* with Phytase BP-17 Expression Cassette Freshly harvested spores of endo glucosaminidase deleted strain of *T. reesei* were suspended in ice-cold 1.2 M sorbitol, washed twice with the same solution and subjected to electroporation with the phytase BP-17 expression cassette. The electroporation parameters were as follows: voltage: −16 kV/cm; capacitance: −25 μF; resistance: −50Ω. Following electroporation, the spores were plated on a selective medium containing acetamide as a sole source of nitrogen (acetamide 0.6 g/l; cesium chloride 1.68 g/l; glucose 20 g/l; potassium dihydrogen phosphate 15 g/l; magnesium sulfate heptahydrate 0.6 g/l; calcium chloride dehydrate 0.6 g/l; iron (II) sulfate 5 mg/l; zinc sulfate 1.4 mg/l; cobalt (II) chloride 1 mg/l; manganese (II) sulfate 1.6 mg/l; agar 20 g/l; pH 4.25). Transformed colonies appeared in about 1 week. Individual transformants were transferred onto fresh acetamide selective plates and allowed to grow for 2-4 days.

Isolates exhibiting stable growth on selective medium were used to inoculate 0.17 ml of lactose defined medium ($(NH_4)_2SO_4$ 5 g/l; PIPPS buffer 33 g/l; Bacto Casamino Acids 9 g/l; $KH_2PO_4$ 4.5 g/l; $CaCl_2*2H_2O$ 1.32 g/l; $MgSO_4*7H_2O$ 1 g/l; Mazu DF204 5 ml/l; 400× Trace Elements 2.5 ml/l; pH 5.5; lactose (sterilized separately) 16 g/l. 400× Trace Elements solution: Citric acid (anhydrous) 175 g/l; $FeSO_4*7H_2O$ 200 g/l; $ZnSO_4*7H_2O$ 16 g/l; $CuSO_4*5H_2O$ 3.2 g/l; $MnSO_4*4H_2O$ 1.4 g/l; $H_3BO_3$ 0.8 g/l.) in wells of micro titer plates equipped with micro filters at the bottoms of the wells (Millipore MultiScreen-GVT™). The plates were incubated for 4-5 days at 25-28 C in an atmosphere of pure oxygen.

The culture medium was separated by filtration and analyzed by polyacrylamide gel electrophoresis in the presence of sodium dodecylsulfate (SDS-PAGE). A new protein band was observed with a mobility expected for a protein slightly larger than that predicted by the amino acid sequence of BP-17. The higher observed molecular weight was assumed to be due to glycosylation. A transformant that produced a high amount of phytase was identified. Phytase produced by this transformant in 14 L bioreactors using the methods described in WO2004/035070 was used in subsequent studies.

Example 3

Generation of Glycosylation Mutants of Phytase BP-17

The phytase BP-17 amino acid sequence contains three potential N-linked glycosylation sites according to analysis by the NetNGlyc 1.0 prediction algorithm (http://www.cb-s.dtu.dk/services/NetNGlyc/). These glycosylation sites are residues N169, N173 and N285 of the mature phytase BP-17 sequence of SEQ ID NO:1 (with reference to the position numbering of SEQ ID NO:1).

Mutations were introduced into the DNA of the phytase BP-17 coding region using a site-directed mutagenesis method. Plasmid pENTRY/D TOPO containing the signal sequence and phytase BP-17 open reading frame, as described in Example 1, was used as template for PCR using primers designed to introduce changes in the BP-17 DNA sequence. The mutations were intended to introduce new glycosylation sites on the surface of the BP-17 molecule.

Each BP-17 variant thus has changes in the amino acid sequence that introduce a new Asn-Xaa-Ser/Thr motif known to be recognized as an N-linked glycosylation site. Seven different variants is of BP-17 were produced. The table below lists the amino acid changes and the oligonucleotides that were used for site-directed mutagenesis. Amino acid numbering is based on the mature BP-17 sequence (SEQ ID NO:1)

| BP-17 Variant | Oligonucleotides used for mutagenesis |
|---|---|
| E121T | E121T(SEQ ID NO: 34): 5'-TCCACCACCAGCAGAACCTCACCAAGGCCGACCCCCTCTTCCAC<br>E121T-r(SEQ ID NO: 35): 5'-GTGGAAGAGGGGGTCGGCCTTGGTGAGGTTCTGCTGGTGGTGGA |
| P394N | P394N(SEQ ID NO: 36): 5'-AGACCGCCGAGGGCTACTGCAACCTCAGCACCTTCACCCGCG<br>P394N-r(SEQ ID NO: 37): 5'-CGCGGGTGAAGGTGCTGAGGTTGCAGTAGCCCTCGGCGGTCT |
| D386N | D386N(SEQ ID NO: 38): 5'-TCAAGATCCCCGGCTGCAACAACCAGACCGCCGAGGGCTAC<br>D386N-r(SEQ ID NO: 39): 5'-GTAGCCCTCGGCGGTCTGGTTGTTGCAGCCGGGGATCTTGA |
| K202N N204T | K202NN204T(SEQ ID NO: 40): 5'-CCCAGCAAGCTCAGCATCAACGACACCGGCAACGAGGTCTCCCTCG<br>K202NN204T-r(SEQ ID NO: 41): 5'-CGAGGGAGACCTCGTTGCCGGTGTCGTTGATGCTGAGCTTGCTGGG |
| Q151N P153S | Q151NP153S(SEQ ID NO: 42): 5'-AGGCCGTCGAGAAGGAGGCCAACACCAGCATCGACAACCTCAACCAGC<br>Q151NP153S-r(SEQ ID NO: 43): 5'-GCTGGTTGAGGTTGTCGATGCTGGTGTTGGCCTCCTTCTCGACGGCCT |
| P373T | BP17P373T(SEQ ID NO: 44): 5'-CCCCCCTCAGCCTCAACCAGACCGCCGGCAGCGTCCAGCTCAAG<br>BP17P373T-r(SEQ ID NO: 45): 5'-CTTGAGCTGGACGCTGCCGGCGGTCTGGTTGAGGCTGAGGGGGG |
| Q76N | BP17R76N(SEQ ID NO: 46): 5'-AGCAGCAGGGCATCCTCAGCAACGGCTCGTGCCCCACCCCC<br>BP17R76N-r(SEQ ID NO: 47): 5'-GGGGGTGGGGCACGAGCCGTTGCTGAGGATGCCCTGCTGCT |

PCR conditions for site-directed mutagenesis were as follows. The PCR mix contained 37 ul H$_2$O, 5 ul 10× PfuUltra II reaction buffer, 2 ul 10 mM dNTP mix, 1 ul (9 ng) pENTR/D TOPO BP-17, 2 ul of 10 uM oligonucleotide 1, 2 ul of 10 uM oligonucleotide 2, 1 ul (2.5 units) PfuUltra II Fusion HS DNA polymerase (Stratagene). PCR conditions were 30 seconds at 95 C; followed by 18 cycles of 30 seconds at 95 C, 1 minute at 55 C, 8 minutes at 68 C. After PCR 1 ul of DpnI restriction endonuclease was added and incubated for 1 hour at 37 C. The PCR product was purified using a Qiagen PCR purification column according to the manufacturer's directions. Finally, *E. coli* cells (One Shot TOP10 chemically competent *E. coli*, Invitrogen) were transformed with the PCR product.

Following site-directed mutagenesis, individual clones of pENTR/D TOPO with the different BP-17 variants were subjected to DNA sequence analysis to confirm that the expected mutations had been accomplished. Each pENTR/D-TOPO vector with the verified sequence of a phytase BP-17 variant open reading frame was recombined with the pTrex3g vector using LR clonase II (Invitrogen) according to the manufacturer's instructions to create pTrex3g/BP-17E121T, pTrex3g/BP-17P394N, pTrex3g/BP-17D386N, pTrex3g/BP-17K202N N204T, pTrex3g/BP-17Q151N P153S, pTrex3g/BP-17P373T, and pTrex3g/BP-17Q76N.

The amino acid sequences of the seven different mature BP-17 variants are disclosed as SEQ ID NO:5 (E121T), SEQ ID NO:6 (P394N), SEQ ID NO:7 (D386N). SEQ ID NO:8 (K202N and N204T), SEQ ID NO:9 (Q151N and P153S), SEQ ID NO:10 (P373T) and SEQ ID NO:11 (Q76N). In each case the amino acid changes relative to BP-17 are shown in brackets, with reference to the position numbering of SEQ ID NO:1.

The resulting different BP-17 variant expression vectors were inserted into the endo glucosaminidase-deleted strain (ETD strain) of *T. reesei* using Biolistic PDS-1000/He Particle Delivery System from Bio-Rad (Hercules, Calif.). The transformation protocol used was as described by Foreman (WO 2005/001036). The selective medium used to isolate transformants contained acetamide as a sole source of nitrogen (acetamide 0.6 g/l; cesium chloride 1.68 g/l; glucose 20 g/l; potassium dihydrogen phosphate 15 g/l; magnesium sulfate heptahydrate 0.6 g/l; calcium chloride dehydrate 0.6 g/l; iron (II) sulfate 5 mg/l; zinc sulfate 1.4 mg/l; cobalt (II) chloride 1 mg/l; manganese (II) sulfate 1.6 mg/l; agar 20 g/l; pH 4.25). Transformed colonies appeared in about 5 days. Individual transformants were transferred onto fresh acetamide selective plates and allowed to grow for 2-4 days.

Isolates exhibiting stable growth on selective medium were used to inoculate 0.17 ml of lactose defined medium (NH$_4$)$_2$SO$_4$ 5 g/l; PIPPS buffer 33 g/l; Bacto Casamino Acids 9 g/l; KH$_2$PO$_4$ 4.5 g/l; CaCl$_2$*2H$_2$O 1.32 g/l; MgSO$_4$*7H$_2$O 1 g/l; Mazu DF204 5 ml/l; 400× Trace Elements 2.5 ml/l; pH 5.5; lactose (sterilized separately) 16 g/l. 400× Trace Elements solution: Citric acid (anhydrous) 175 g/l; FeSO$_4$*7H$_2$O 200 g/l; ZnSO$_4$*7H$_2$O 16 g/l; CuSO$_4$*5H$_2$O 3.2 g/l; MnSO$_4$*4H$_2$O 1.4 g/l; H$_3$BO$_3$ 0.8 g/l.) in wells of micro titer plates equipped with micro filters at the bottoms of the wells (Millipore MultiScreen-GVT™). The plates were incubated for 4-5 days at 25 C-28 C in an atmosphere of pure oxygen. The culture medium was separated by filtration and analyzed by polyacrylamide gel electrophoresis in the presence of sodium dodecylsulfate (SDS-PAGE). A new protein band was observed with a mobility expected for a protein slightly larger than that predicted by the amino acid sequence of BP-17. The higher observed molecular weight was assumed to be due to glycosylation.

Figure 2:
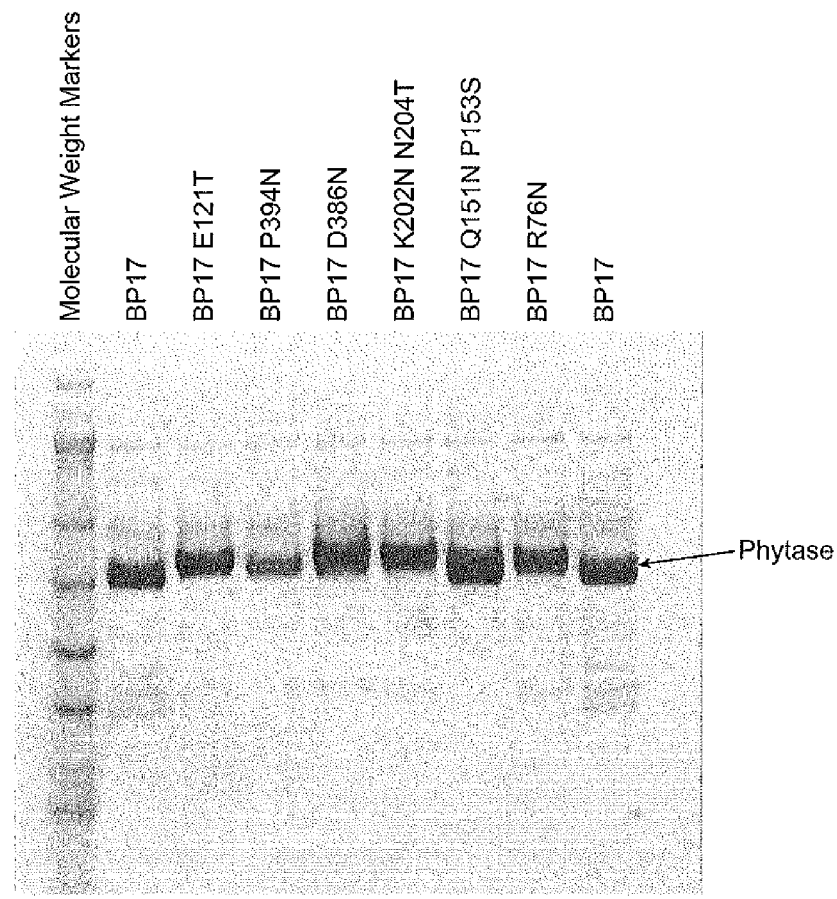
FIG. 2 provides a comparison of molecular weight of variant phytases.

One transformant with each different BP-17 variant that produced a high amount of phytase was selected. Supernatant from each of these BP-17 variant transformants was compared to supernatant containing phytase BP17-ETD, produced in the ETD strain, by SDS-PAGE (FIG. 2). As judged by the mobility of the phytase band on SDS-PAGE the different BP-17 variants all had increased glycan content relative to BP17-ETD but to different degrees. Two of the BP-17 variants (D386N and K202N N204T) that showed the greatest increase in apparent molecular weight on SDS-PAGE relative to BP17-ETD were chosen. Phytase produced by these two transformants in 14 L bioreactors using the methods described in WO2004/035070 was used in subsequent studies.

Site-directed mutagenesis reactions were also performed to create DNA encoding BP-17 variants having two additional N-linked glycosylation sites. Plasmid pENTR/D TOPO with the BP-17 variant D386N was used as the template in site-directed mutagenesis reactions with primer pairs E121T and E121T-r, or K202NN204T and K202NN204T-r, or BP17R76N and BP17R76N-r using the conditions described above. In this way the BP-17 variants D386N E121T, D386N K202N N204T, and D386N Q76N were synthesized and inserted into the expression vector pTrex3g.

Plasmid pENTR/D TOPO with the BP-17 variant Q76N was used as the template in site-directed mutagenesis reactions with primer pair K202NN204T and K202NN204T-r using the conditions described above. In this way the BP-17 variant Q76N K202N N204T was synthesized and inserted into the expression vector pTrex3g.

The resulting different BP-17 variant expression vectors were inserted into the ETD strain of *T. reesei* using Biolistic PDS-1000/He Particle Delivery System as described above. *T. reesei* transformants were identified that produced BP-17 variants D386N E121T, D386N K202N N204T, D386N Q76N, and Q76N K202N N204T in liquid culture. These variants each have two additional N-linked glycosylation sites compared to BP-17.

Using similar techniques, one can create BP-17 variants with three or more additional N-linked glycosylation sites compared to BP-17.

Example 4

Extent of Glycosylation Determined by Mass Spectrometry

A mass spectrometric study was conducted to further characterize the glycosylation found on phytase BP-17 (SEQ ID NO:1) produced in *T. reesei* (BP17-native) compared to BP-17 produced in *T. reesei* with the endo glucosaminidase gene deletion (BP17-ETD). Additionally, phytase BP-17 variants D386N (SEQ ID NO:7) and K202N N204T (SEQ ID NO:8), both produced in the ETD strain, were characterized.

Protein N-linked De-glycosylation (Endo-H) Reaction

N-deglycosylation of all BP-17 samples was enzymatically carried out using Endoglycosidase H (Endo-H, Endo-β-N-acetylglucosaminidase H) in 50 mM sodium acetate, pH 5.5. 2.0 mg/mL of Endo-H was added to the phytase solution with protein ratio at 1/100 (w/w). The deglycosylation reaction was performed at 37 C for 2-3 hours. The reacted protein samples were subjected to a ZipTip® (Micro C4 reversed-phase column) (Millipore, Bedford, Mass.) cleanup step prior to MALDI-TOF/MS analysis according to a standard protocol suggested by the vendor (www.millipore.com). The endoH digestion removes the N-linked glycan chain except for a single N-acetyl glucosamine (203 Da) that remains attached to the asparagine residue of the protein at the site of glycosylation.

MALDI-TOF/MS Analysis for Intact Protein MW Determination

Desalted protein samples were prepared for MALDI-TOF/MS analysis by co-crystallizing an equal volume (1 μL) of sample with Sinapinic acid matrix (saturated in 50% acetonitrile, 0.1% formic acid) using the dried droplet method. Protein mass spectra were obtained using a Voyager DE-STR MALDI-TOF mass spectrometer (Applied Biosystems, Foster City, Calif., USA). The MS instrument settings for the 20000-80000 m/z range were linear mode of operation, delayed extraction mode, positive polarity, 25 kV acceleration voltage, 93% grid voltage, and 750 nsec extraction delay time. 300-laser shots/spectrum and BSA was used as external calibrant.

Using MALDI-TOF/MS analysis a comparison was made between BP17-native, BP17-ETD and the BP-17 variants produced in the ETD strain before and after endoH digestion. In each sample there was a population of phytase proteins that varied in mass due to heterogeneity of the glycosylation. However, a major species could be identified for each sample indicating likely differences in the total mass of N-linked glycan between samples. Phytase (BP-17) produced in *T. reesei* with and without endo glucosaminidase gene deletion are both glycosylated but the degree of glycosylation is different (Table 1). The major BP17-ETD molecule showed an approximately 900 Da increase in mass compared to BP17-native (47,254 Da compared to 48,127 Da) hypothesized to be due to increased mass of the attached N-linked glycans. The extent of glycosylation was even greater for the BP-17 variants produced in the endo glucosaminidase-delete strain with the total mass of the enzymes being approximately 50,000 Da.

LC/MS (Diphenyl Column) Analysis for Accurate Protein (BP-17) MW Determination

All MS data were acquired using a Surveyor™ LC system coupled to an LCQ Advantage MS system (ThermoFinnigan, San Jose, Calif.). A Vydac Diphenyl column (2.1×150 mm) was used for all BP-17 samples using the HPLC gradient from 0% to 70% Solvent B over 40 minutes at a flow rate of 200 μL/min. Solvent A: 0.1% TFA in water and Solvent B: 0.08% TFA in acetonitrile. Data Processing was performed using Xcalibur software program (ThermoFinnigan, San Jose, Calif.) and the MagTran program for protein intact mass deconvolution.

LC/MS was used to obtain a more accurate mass of the phytase protein after endoH digestion to remove the glycosylation. With the Endo-H treatment, both BP17-native and BP17-ETD samples displayed two phytase species with molar mass of 45815 Da and 46020 Da that are equivalent to the BP-17 amino acid sequence (theoretical molecular weight of 45410.8) with 2 and 3 N-acetyl glucosamines (GlcNAc) attached. This supports the hypothesis that initially some phytase molecules had N-linked glycans attached to two positions on the surface and some molecules had N-linked glycans attached to three positions on the surface.

The two BP-17 variants (D386N and K202N N204T), after endoH digestion, displayed molar masses equivalent to the BP-17 amino acid sequence with 3 and 4 N-acetyl glucosamines (GlcNAc) attached. As noted above, after endoH treatment BP-17 displayed molar masses equivalent to the BP-17 amino acid sequence with 2 and 3 GlcNAc residues attached. Thus, it was confirmed that the two variant BP-17 molecules each had one additional N-linked glycan attached to the surface compared to BP17-native and BP17-ETD.

Table 1 summarizes the distribution and identified molecular weights of various species found in each sample using the MALDI-TOF/MS and the LC/MS techniques.

TABLE 1

MS analysis of various BP-17 and BP-17_ETD samples with and without the Endo-H treatment.

| | MALDI-TOF/MS | | | LC/MS |
|---|---|---|---|---|
| Sample | Mass of major species before endoH treatment (Da) | Mass of major species after endoH treatment (Da) | Calculated mass of glycan released by endoH treatment (Da) | Mass of major species after endoH treatment (Da) |
| BP17-native | 47254* | 45925* | 1329* | 45816* |
| | | | | 46018* |
| BP17-ETD | 48127* | 45901* | 2225* | 45818* |
| | | | | 46021* |
| BP17 K202N N204T | 49977 | 45991 | 3986 | 45998 |
| | | | | 46192 |
| BP17 D386N | 50056 | 46062 | 3994 | 46007 |
| | | | | 46210 |

*Average of measurements from three independent samples

Example 5

Enzymology

The following procedure was used to purify phytase BP17-native and phytase BP17-ETD. Concentrated fermentation supernatant (50 ml) was applied to a 600 mL desalting chromatography column (GE Healthcare PN 17-0034-02, G-25 coarse media) equilibrated with 25 mM sodium acetate, pH 5.0 buffer. The desalted sample (150 mL) was diluted 10 fold to 1500 mL with ultrapure water and loaded onto a 90 ml cation-exchange chromatography column (GE Healthcare PN 17-1087-01, SP Sepharose HP). After washing with 25 mM sodium acetate, pH 5.0 buffer, the phytase was eluted using a gradient from the base buffer to 200 mM sodium chloride in 25 mM sodium acetate, pH 5.0 buffer. Phytase eluted at a sodium chloride concentration of 150-175 mM. The phytase fractions were pooled, concentrated and buffer exchanged with 50 mM sodium acetate, pH 5.5 buffer (using the desalting column as above), and concentration and purity were determined. Phytase samples were found to be >95% pure using this procedure.

Phytase activity was determined in 96-well microtiter plates (MTP's) using enzymatic assays, as follows.

Unless otherwise noted, all phytase samples were diluted to 0.153 mg/mL in sodium acetate (NaOAc) buffer containing 0.25 M NaOAc (pH 5.5), 1.3 mM CaCl2, and 0.01% Tween 20. Where noted, conductivity was balanced at 12 mS/cm using 2M NaCl and pH rebalanced. Activity of phytase samples was determined in 96-well MTP plates by an enzymatic pNPP (para-Nitro Phenyl Phosphate, Sigma Chemical) assay. pNPP was made to 60 mM in NaOAc buffer (pH 5.5). If needed, samples were centrifuged at 2500 rpm for 2 minutes to remove any precipitates. 15 uL of phytase sample was added to 96-well MTP's using followed by 181 uL of 60 mM pNPP (equilibrated at 30° C). MTP plates were read kinetically using a spectrophotometer (Spectromax) pre-set to 30 C at an absorbance of 430 nm.

Inactivity Reversibility Assay.

100 μL samples of 0.153 mg/mL phytase were added to PCR tubes. Samples were then heat treated at various incubation temperatures up to 95 C using a PCR thermocycler. Samples were collected after 10 minutes and cooled and kept on ice until time of assay. After all samples had been collected, remaining activity was assessed by pNPP assays at 30 C.

Figure 3:
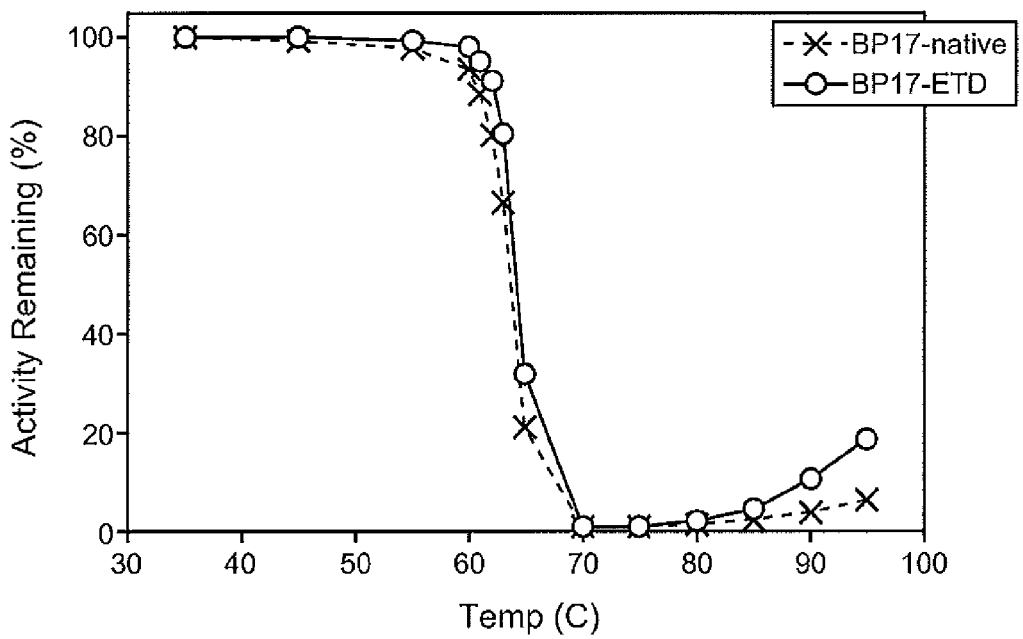
FIG. 3 provides an analysis on the BP17 samples produced from *T. reesei*, with BP17 samples produced from the endo-N-acetyl glucosaminidase gene deleted *T. reesei*.

In stability studies with phytase BP-17 it was observed that at temperatures above approximately 70 C the remaining activity of some of the phytase samples surprisingly improved with increasing temperature (FIG. 3). This improved activity following treatment at more elevated temperatures (see especially 90 C and 95 C) was more pronounced for the BP-17-ETD phytase than the BP17 native. Deletion of the endo glucosaminidase gene led to substantially improved activity of the phytase BP17-ETD. This supports the hypothesis that inactivity reversibility can correlate with extent of glycosylation, and glycosylation can be related to expression host.

Apparent Melting Temperature ($Tm_{app}$)

The apparent melting temperature ($Tm_{app}$) values for BP17-native and BP17-ETD at pH 4.0 and pH 5.5 were calculated from stability studies (pH 4.0 study shown in FIG. 3) and are shown in Table 2. Expression host did not significantly affect $Tm_{app}$, as shown by the observation that BP17-native or BP17-ETD produced in the ETD strain had the same $Tm_{app}$.

TABLE 2

Apparent melting temperature ($Tm_{app}$) values for BP17 at pH 4.0 and pH 5.5. (Percent remaining activity at 95 C. in brackets.)

| | Tm ° C./reversibility [Remaining Activity] | |
|---|---|---|
| Sample (host strain) | pH 4.0 | pH 5.5 |
| BP17-native | ~63 [~6%] | 70 |
| BP17-ETD | ~63 [~19%] | 70 |

Rate of Inactivity Reversibility of Phytases

In order to characterize the timing of the changes in phytase activity, stability studies were performed and remaining activity of samples measured as a function of time following removal from heat.

Figure 4:
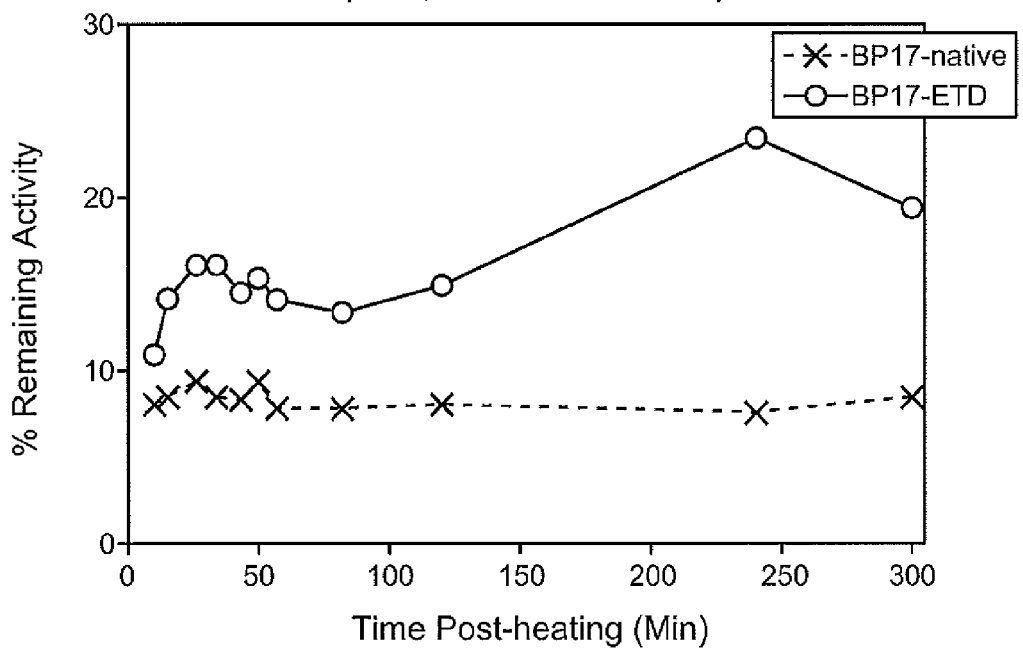
FIG. 4 provides an inactivity reversibility study showing percent activity remaining of BP-17, expressed in different hosts, held at 95 C for 10 minutes at pH 4.0.

FIG. 4 shows percent remaining activity of BP17-native and BP17-ETD as a function of time after treatment at 95 C for 10 minutes, and removal to room temperature to be measured at the various indicated time-points over 5 hours sitting at room temperature. These values are percentages calculated relative to an unheated control sample.

BP17-native did not show any increase in activity at room temperature. However, BP17-ETD showed increased activity reaching 19% of the activity of the untreated sample, an 8.5% increase over the initial timepoint immediately after heat treatment.

Samples did not gain further activity after 24 or 48 hrs when kept at 4 C (data not shown).

Example 6

Fluid Bed Granulation and Pelleting Trials

Phytase was incorporated into granules, a process generally understood to provide some protection against subsequent steam treatment. These enzyme granules were then mixed with animal feed and passed through an animal feed pelleter that incorporated a steam treatment. It is desirable for the phytase enzyme to retain activity following this pelleting process.

To determine phytase enzyme stability during the pelleting process, enzyme granules were produced using a fluid-bed spray process described in U.S. Pat. No. 5,324,649. Sodium sulfate seeds (also referred to as the core) were charged into a fluid bed chamber. The "spray 1" solution was prepared by dissolving or dispersing sucrose, and corn starch into ultrafiltered phytase concentrate (UFC). Additional water was added to this mixture in order to keep the total concentration of solids about 40%. Constant stirring was required in order to keep the corn starch and paraffin oil or antifoam well dispersed in the enzyme UFC.

Spray 1 was applied to the sodium sulfate core already charged to the fluid bed granulator using a top spray process. The temperature, spray rate, atomization air pressure and other parameters were all adjusted in order to obtain a good yield of spray 1 coating onto the core without agglomerating the particles.

Subsequent sprays (Spray 2, Spray 3, etc.) were prepared by dissolving and/or dispersing all of the components of this spray solution into water so as to form a solution containing approximately 18 to 40% solids. Sprays containing water insoluble oil, antifoam or corn starch required continuous stirring order to keep these materials well dispersed.

Granules were harvested after the final spray and phytase activity was determined using a phytase assay.

The multi-layered granules were then combined with a mixture of 60% corn meal and 40% soy meal (i.e. the mash) at a ratio of 60 grams of granules to 120 kilograms of corn-soy meal such that the final activity of phytase in the mixture before pelleting was approximately 5 units/gram.

This mixture was then pelleted in an animal feed pelleter. The granules and the corn-soy meal were blended in a horizontal ribbon mixer, for approximately 15 minutes. The pellet mill was a Simon Heesen, mono roll type, fitted with a 17.3 cm inner diameter die, with a pellet hole diameter of 3 mm. Die speed was 500 rpm and was driven by a 7.5 kW motor. The typical feed rate was 300 kg per hour. The temperature in the conditioner was kept at +/−0.1 degrees Celsius, measured at the feed outlet from the conditioner. The conditioner had a cascade type mixer system. Two conditioning temperatures were used: 90 C, and 95 C. Steam inlet pressure was 2 atm, and the temperature in the conditioner was controlled by manual adjustment of three valves that regulate the steam delivery. The residence time in the conditioner was approximately 30 seconds. When the target temperature was reached, the system was run for approximately 5 to 10 minutes before sampling took place. Samples were taken for 1-1.5 minute periods, corresponding to 5-7.5 kg of pelleted feed, and were immediately placed in a cooling box with a perforated bottom and air flow of 1500 cubic meters per hour. After cooling for 15 minutes, the samples were downsized twice using a sample divider, and 1 kg was taken for lab tests.

After pelleting and cooling, the pellets were then ground up and assayed for phytase activity. The unpelleted mixture of corn-soy meal and phytase granule is called the "mash" control and was also assayed for phytase activity. The ratio of recovered activity in the enzyme granule pelleted at either 90 C or 95 C to the mash control activity is the percent recovered activity.

Lab Scale Granulation and Pelleting

Table 3 summarizes the granule formulations made and tested in pelleting trials. Approximately 720 grams of sodium sulfate seeds were charged to the coater and the various spray solutions were prepared and sprayed as described above to make the granules. The mass of the finished batch of granules was approximately 2,000 grams.

TABLE 3

|  | V-09-107<br>BP17-native | V-09-203<br>BP17-ETD |
| --- | --- | --- |
| Spray 1 |  |  |
| Enzyme Solids | 4.77% | 4.84% |
| PVA | 1.00% | 1.00% |
| Starch | 3.00% | 5.00% |
| Spray 2 |  |  |
| Na2SO4 | 40.00% | 40.00% |
| Spray 3 |  |  |
| Talc | 6.00% | 6.00% |
| PVA | 3.00% | 3.00% |
| Core |  |  |
| Na2SO4 | 42.23% | 40.16% |

TABLE 4

|  | V-11-144<br>BP17-ETD | L-11-144<br>BP17-D386N<br>ETD | L-11-145<br>BP17-K202N<br>N204T ETD |
| --- | --- | --- | --- |
| Spray 1 |  |  |  |
| Enzyme Solids | 4.44% | 5.73% | 5.23% |
| Sucrose | 3.00% | 3.00% | 3.00% |
| Starch | 6.50% | 6.50% | 6.50% |
| Rapeseed Oil | 0.75% | 0.75% | 0.75% |
| Spray 2 |  |  |  |
| Na2SO4 | 40.00% | 40.00% | 40.00% |
| Spray 3 |  |  |  |
| Talc | 6.00% | 6.00% | 6.00% |
| PVA | 3.00% | 3.00% | 3.00% |
| Core |  |  |  |
| Na2SO4 | 36.31% | 35.02% | 35.52% |

Results

Figure 5:
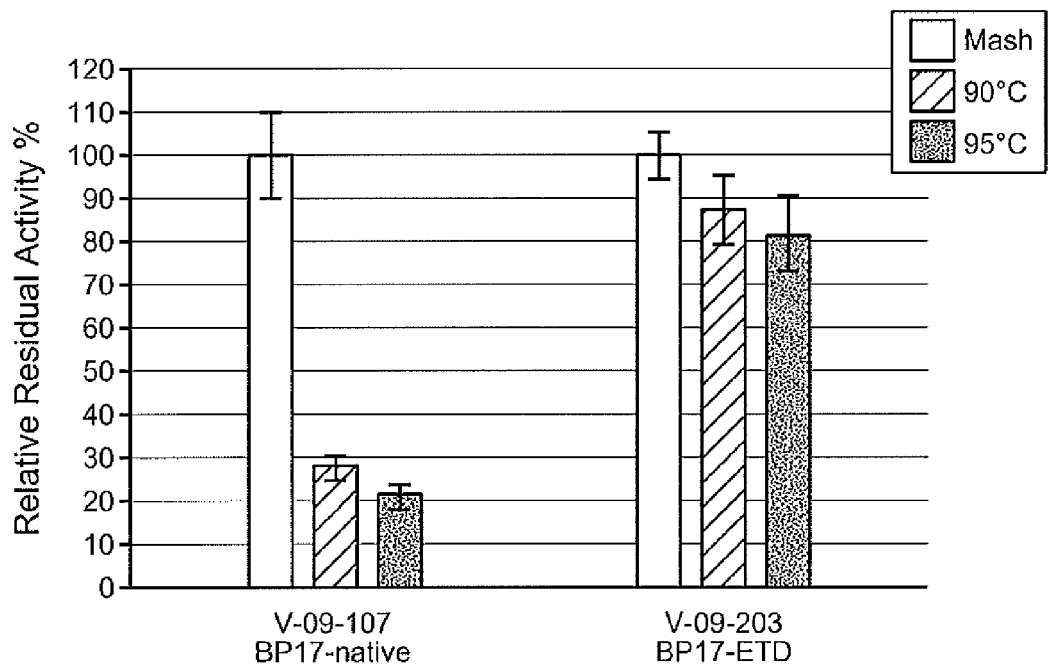
FIG. 5 provides the percent remaining activity of BP-17 (produced from *T. reesei*) and BP-17 (produced from *T. reesei* having the endo-N-acetyl glucosaminidase gene deleted) as a function of time after treatment at 95 C for 10 minutes.

The recovered activity obtained after pelleting the formulations in Table 3 at both 90 C and 95 C is plotted in FIG. 5. Here, it can be seen that the BP17-ETD phytase results in an increase in recovered activity at both 90 C and 95 C. BP17-native phytase, on the other hand, showed a substantial decrease in activity post-pelleting. (The small difference in starch levels or enzyme solids in the formulations of Table 3 would have very little impact on the pelleting performance of these formulations.)

Figure 6:
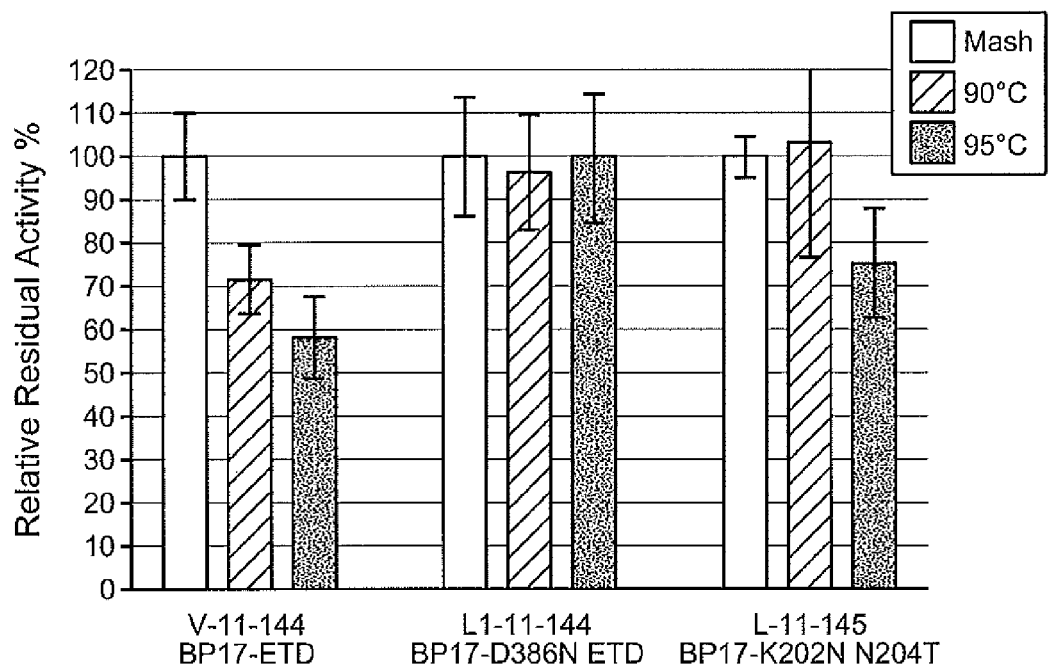
FIG. 6 provides a graph showing the recovered activity obtained after pelleting the granule formulations of Table 3 at both 90 C and 95 C.

The recovered activity obtained after pelleting the formulations in Table 4 at both 90 C and 95 C is plotted in FIG. 6. Here, it can be seen that the effect of additional glycosylation due to creation of additional glycosylation sites on the BP17 protein is again an increase in recovered activity at both 90 C and 95 C. (The small differences in enzyme solids levels in the formulations of Table 4 would have very little impact on the pelleting performance of these formulations.)

Although the foregoing compositions and methods have been described in some detail by way of illustration and examples for purposes of clarity of understanding, it will be apparent to those skilled in the art that certain changes and modifications may be made. Therefore, the description should not be construed as limiting the scope of the present teachings, which is delineated by the appended claims.

All publications, patents, and patent applications cited herein are hereby incorporated by reference in their entireties for all purposes and to the same extent as if each individual publication, patent, or patent application were specifically and individually indicated to be so to incorporated by reference.

```
                         SEQUENCE LISTING

<160> NUMBER OF SEQ ID NOS: 47

<210> SEQ ID NO 1
<211> LENGTH: 413
<212> TYPE: PRT
<213> ORGANISM: Artificial Sequence
<220> FEATURE:
<223> OTHER INFORMATION: Synthetic construct: BP17, a variant phytase
      comprising 12 amino acid substitutions compared to the wild type
      (SEQ ID NO:4), lacking the signal sequence (SEQ ID NO:12)

<400> SEQUENCE: 1

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270
```

```
Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

<210> SEQ ID NO 2
<211> LENGTH: 413
<212> TYPE: PRT
<213> ORGANISM: Artificial Sequence
<220> FEATURE:
<223> OTHER INFORMATION: Synthetic construct: BP11, a variant phytase
      comprising 11 amino acid substitutions compared to the wild type
      (SEQ ID NO:4), lacking the signal sequence (SEQ ID NO:12)

<400> SEQUENCE: 2

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65              70                  75                  80

Thr Pro Asn Ser Ile Tyr Val Trp Thr Asp Val Asp Gln Arg Thr Leu
            85                  90                  95

Lys Thr Gly Glu Ala Phe Leu Ala Gly Leu Ala Pro Gln Cys Gly Leu
        100                 105                 110

Thr Ile His His Gln Gln Asn Leu Glu Lys Ala Asp Pro Leu Phe His
    115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
            165                 170                 175

Ser Pro Trp Cys Gln Lys His Ser Ala Asp Lys Ser Cys Asp Leu Gly
        180                 185                 190

Leu Ser Met Pro Ser Lys Leu Ser Ile Lys Asp Asn Gly Asn Glu Val
    195                 200                 205
```

```
Ser Leu Asp Gly Ala Ile Gly Leu Ser Ser Thr Leu Ala Glu Ile Phe
    210             215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
                260                 265                 270

Pro Leu Leu Gln Ala Ile Ser Asn Ala Leu Asn Pro Asn Ala Thr Glu
                275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
                355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

<210> SEQ ID NO 3
<211> LENGTH: 413
<212> TYPE: PRT
<213> ORGANISM: Artificial Sequence
<220> FEATURE:
<223> OTHER INFORMATION: Synthetic construct: BP111, a variant phytase
      comprising 21 amino acid substitutions compared to the wild type
      (SEQ ID NO:4), lacking the signal sequence (SEQ ID NO:12)

<400> SEQUENCE: 3

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Pro Arg Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
        130                 135                 140

Ala Val Glu Lys Glu Ala Gln Thr Pro Ile Asp Asn Leu Asn Gln Arg
```

```
145                 150                 155                 160

Tyr Ile Pro Glu Leu Ala Leu Met Asn Thr Ile Leu Asn Phe Ser Lys
                165                 170                 175

Ser Pro Trp Cys Gln Lys His Ser Ala Asp Lys Pro Cys Asp Leu Ala
                180                 185                 190

Leu Ser Met Pro Ser Lys Leu Ser Ile Lys Asp Asn Gly Asn Glu Val
                195                 200                 205

Ser Leu Asp Gly Ala Ile Gly Leu Ser Ser Thr Leu Ala Glu Ile Phe
                210                 215                 220

Leu Leu Glu Tyr Ala Gln Gly Met Pro Gln Val Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
                260                 265                 270

Pro Leu Leu Gln Ala Ile Ser Asn Ala Leu Asn Pro Asn Ala Thr Glu
                275                 280                 285

Ser Lys Leu Pro Asp Ile Ser Pro Asp Asn Lys Ile Leu Phe Ile Ala
                290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
                355                 360                 365

Ser Leu Asn Gln Pro Pro Gly Ser Val Gln Leu Lys Ile Pro Gly Cys
                370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 4
<211> LENGTH: 413
<212> TYPE: PRT
<213> ORGANISM: Buttiauxella sp.
<220> FEATURE:
<221> NAME/KEY: misc_feature
<223> OTHER INFORMATION: Wild type phytase encoded by Buttiauxella sp.
      strain P 1-29 deposited under accession number NCIMB 41248,
      lacking the signal sequence (SEQ ID NO:12)

<400> SEQUENCE: 4

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
                35                  40                  45

Ile Thr Pro Arg Gly Glu His Leu Ile Ser Leu Met Gly Gly Phe Tyr
                50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
```

```
                        85                  90                  95
Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Thr Cys Ser Met Asp Lys Thr Gln Val Gln Gln
        130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 5
<211> LENGTH: 413
<212> TYPE: PRT
<213> ORGANISM: Artificial Sequence
<220> FEATURE:
<223> OTHER INFORMATION: Synthetic construct: BP17 with an additional
      amino acid substitution E121T

<400> SEQUENCE: 5

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30
```

```
Asp Val Thr Pro Asn Thr Trp Pro Glu Trp Pro Val Lys Leu Gly Tyr
             35                  40                  45

Ile Thr Pro Arg Gly Glu His Leu Ile Ser Leu Met Gly Gly Phe Tyr
 50                  55                  60

Arg Gln Lys Phe Gln Gln Gln Gly Ile Leu Ser Gln Gly Ser Cys Pro
 65                  70                  75                  80

Thr Pro Asn Ser Ile Tyr Val Trp Thr Asp Val Ala Gln Arg Thr Leu
                 85                  90                  95

Lys Thr Gly Glu Ala Phe Leu Ala Gly Leu Ala Pro Gln Cys Gly Leu
                100                 105                 110

Thr Ile His His Gln Gln Asn Leu Thr Lys Ala Asp Pro Leu Phe His
             115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
                180                 185                 190

Leu Ser Met Pro Ser Lys Leu Ser Ile Lys Asp Asn Gly Asn Glu Val
            195                 200                 205

Ser Leu Asp Gly Ala Ile Gly Leu Ser Ser Thr Leu Ala Glu Ile Phe
            210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
                260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 6
<211> LENGTH: 413
<212> TYPE: PRT
<213> ORGANISM: Artificial Sequence
<220> FEATURE:
<223> OTHER INFORMATION: Synthetic construct: BP17 with an additional
``` amino acid substitution P394N

<400> SEQUENCE: 6

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
                35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Asn Leu Ser Thr Phe Thr Arg
385                 390                 395                 400

Val Val Ser Gln Ser Val Glu Pro Gly Cys Gln Leu Gln
            405                 410

<210> SEQ ID NO 7
<211> LENGTH: 413
<212> TYPE: PRT
<213> ORGANISM: Artificial Sequence
<220> FEATURE:
<223> OTHER INFORMATION: Synthetic construct: BP17 with an additional
      amino acid substitution D386N

<400> SEQUENCE: 7

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

```
Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
    370                 375                 380

Asn Asn Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 8
<211> LENGTH: 413
<212> TYPE: PRT
<213> ORGANISM: Artificial Sequence
<220> FEATURE:
<223> OTHER INFORMATION: Synthetic construct: BP17 with additional amino
      acid substitutions K202N and N204T

<400> SEQUENCE: 8

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65              70                  75                  80

Thr Pro Asn Ser Ile Tyr Val Trp Thr Asp Val Ala Gln Arg Thr Leu
            85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Asn Asp Thr Gly Asn Glu Val
            195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
            245                 250                 255

Phe Asp Leu Met Glu Arg Thr Pro Tyr Ile Ala Arg His Lys Gly Thr
                260                 265                 270

Pro Leu Leu Gln Ala Ile Ser Asn Ala Leu Asn Pro Asn Ala Thr Glu
    275                 280                 285

Ser Lys Leu Pro Asp Ile Ser Pro Asp Asn Lys Ile Leu Phe Ile Ala
```

```
                    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 9
<211> LENGTH: 413
<212> TYPE: PRT
<213> ORGANISM: Artificial Sequence
<220> FEATURE:
<223> OTHER INFORMATION: Synthetic construct: BP17 with additional amino
      acid substitutions Q151N and P153S

<400> SEQUENCE: 9

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Asn Thr Ser Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240
```

```
His Ser Glu Gln Glu Trp Ala Leu Leu Lys Leu His Asn Val Tyr
            245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
            325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
            370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
            405                 410

<210> SEQ ID NO 10
<211> LENGTH: 413
<212> TYPE: PRT
<213> ORGANISM: Artificial Sequence
<220> FEATURE:
<223> OTHER INFORMATION: Synthetic construct: BP17 with an additional
      amino acid substitution P373T

<400> SEQUENCE: 10

Asn Asp Thr Pro Ala Ser Gly Tyr Gln Val Glu Lys Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
            85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
            165                 170                 175

Ser Pro Trp Cys Gln Lys His Ser Ala Asp Lys Ser Cys Asp Leu Gly
            180                 185                 190
```

```
Leu Ser Met Pro Ser Lys Leu Ser Ile Lys Asp Asn Gly Asn Glu Val
            195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
                260                 265                 270

Pro Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
            355                 360                 365

Ser Leu Asn Gln Thr Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 11
<211> LENGTH: 413
<212> TYPE: PRT
<213> ORGANISM: Artificial Sequence
<220> FEATURE:
<223> OTHER INFORMATION: Synthetic construct: BP17 with an additional
      amino acid substitution Q76N

<400> SEQUENCE: 11

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Asn Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
```

```
            130                 135                 140
Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 12
<211> LENGTH: 33
<212> TYPE: PRT
<213> ORGANISM: Artificial Sequence
<220> FEATURE:
<223> OTHER INFORMATION: Synthetic construct: signal sequence for wild
      type (SEQ ID NO:4)

<400> SEQUENCE: 12

Met Thr Ile Ser Ala Phe Asn Arg Lys Lys Leu Thr Leu His Pro Gly
1               5                   10                  15

Leu Phe Val Ala Leu Ser Ala Ile Phe Ser Leu Gly Ser Thr Ala Tyr
                20                  25                  30

Ala

<210> SEQ ID NO 13
<211> LENGTH: 1274
<212> TYPE: DNA
<213> ORGANISM: Artificial Sequence
<220> FEATURE:
<223> OTHER INFORMATION: Synthetic construct: DNA sequence of BP-17
``` variant of Buttiauxella phytase containing a Spe1 site at the 5'
end, and Asc1 site at the 3' end

<400> SEQUENCE: 13

| | |
|---|---|
| actagtgtcg ccgtggagaa gcgcaacgac acccccgcca gcggctacca ggtcgagaag | 60 |
| gtcgtcatcc tcagccgcca cggcgtccgc gcccctacca agatgaccca gaccatgcgc | 120 |
| gacgtcaccc ccaacacctg gcccgagtgg cccgtcaagc tcggctacat cacccctcgc | 180 |
| ggcgagcacc tcatcagcct catgggcggc ttctaccgcc agaagttcca gcagcagggc | 240 |
| atcctcagcc agggctcgtg ccccaccccc aacagcatct acgtctggac cgacgtcgcc | 300 |
| cagcgcaccc tcaagaccgg cgaggccttc ctcgccggcc tcgcccccca gtgcggcctc | 360 |
| accatccacc accagcagaa cctcgagaag gccgacccc tcttccaccc cgtcaaggcc | 420 |
| ggcatctgca gcatggacaa gacccaggtc cagcaggccg tcgagaagga ggcccagacc | 480 |
| cccatcgaca acctcaacca gcactacatc cccagcctcg ccctcatgaa caccacctc | 540 |
| aacttcagca gagcccctg gtgccagaag cacagcgccg acaagagctg cgacctcggc | 600 |
| ctcagcatgc ccagcaagct cagcatcaag gacaacggca acgaggtctc cctcgacggc | 660 |
| gctatcggcc tcagctccac cctcgccgag atcttcctcc tcgagtacgc ccagggcatg | 720 |
| cctcaggccg cctggggcaa catccacagc gagcaggagt gggccctcct cctcaagctc | 780 |
| cacaacgtct acttcgacct catggagcgc accccctaca tcgcccgcca aagggcacc | 840 |
| cccctcctcc aggccatcag caacgccctc aaccccaacg ccaccgagag caagctcccc | 900 |
| gacatcagcc ccgacaacaa gatcctcttc atcgccggcc acgacaccaa catcgccaac | 960 |
| atcgccggca tgctcaacat gcgctggacc ctccccggcc agcccgacaa cacccccct | 1020 |
| ggcggcgctc tcgtctttga gcgcctcgcc gacaagtccg gcaagcagta cgtcagcgtc | 1080 |
| agcatggtct accagaccct cgagcagctc cgcagccaga ccccctcag cctcaaccag | 1140 |
| cctgccggca gcgtccagct caagatcccc ggctgcaacg accagaccgc cgagggctac | 1200 |
| tgccccctca gcaccttcac ccgcgtcgtc agccagagcg tcgagcccgg ctgccagctc | 1260 |
| cagtaaggcg cgcc | 1274 |

<210> SEQ ID NO 14
<211> LENGTH: 82
<212> TYPE: DNA
<213> ORGANISM: Artificial Sequence
<220> FEATURE:
<223> OTHER INFORMATION: Synthetic primer: SK680 (forward)

<400> SEQUENCE: 14

| | |
|---|---|
| caccatgcag accttcggtg cttttctcgt ttccttcctc gccgccagcg gcctggccgc | 60 |
| ggccaacgac acccccgcca gc | 82 |

<210> SEQ ID NO 15
<211> LENGTH: 18
<212> TYPE: DNA
<213> ORGANISM: Artificial Sequence
<220> FEATURE:
<223> OTHER INFORMATION: Synthetic primer: SK6

<400> SEQUENCE: 15

| | |
|---|---|
| ccttactgga gctggcag | 18 |

<210> SEQ ID NO 16
<211> LENGTH: 21
<212> TYPE: DNA

```
<213> ORGANISM: Artificial Sequence
<220> FEATURE:
<223> OTHER INFORMATION: Synthetic primer: SK745

<400> SEQUENCE: 16
gagttgtgaa gtcggtaatc c                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic primer: SK746

<400> SEQUENCE: 17
ctggaaacgc aaccctgaag                                                20

<210> SEQ ID NO 18
<211> LENGTH: 48
<212> TYPE: DNA
<213> ORGANISM: Artificial Sequence
<220> FEATURE:
<223> OTHER INFORMATION: Synthetic construct: PCR product sequence in
      Example 1, between the cbh1 promoter and the signal sequence
      /BP-17 coding sequence

<400> SEQUENCE: 18
atcacaagtt tgtacaaaaa agcaggctcc gcggccgccc ccttcacc                  48

<210> SEQ ID NO 19
<211> LENGTH: 52
<212> TYPE: DNA
<213> ORGANISM: Artificial Sequence
<220> FEATURE:
<223> OTHER INFORMATION: Synthetic construct: PCR product sequence in
      Example 1, between the 3' end of the BP-17 coding sequence and the
      cbh1 terminator region

<400> SEQUENCE: 19
ggaagggtgg gcgcgccgac ccagctttct tgtacaaagt ggtgatcgcg cc             52

<210> SEQ ID NO 20
<211> LENGTH: 29
<212> TYPE: DNA
<213> ORGANISM: Artificial Sequence
<220> FEATURE:
<223> OTHER INFORMATION: Synthetic primer: SK915

<400> SEQUENCE: 20
ctgatatcct ggcatggtga atctccgtg                                      29

<210> SEQ ID NO 21
<211> LENGTH: 32
<212> TYPE: DNA
<213> ORGANISM: Artificial Sequence
<220> FEATURE:
<223> OTHER INFORMATION: Synthetic primer: SK916

<400> SEQUENCE: 21
catggcgcgc cgaggcagat aggcggacga ag                                  32

<210> SEQ ID NO 22
<211> LENGTH: 31
<212> TYPE: DNA
<213> ORGANISM: Artificial Sequence
<220> FEATURE:
<223> OTHER INFORMATION: Synthetic primer: SK917
```

```
<400> SEQUENCE: 22
catggcgcgc cgtgtaagtg cgtggctgca g                                     31

<210> SEQ ID NO 23
<211> LENGTH: 30
<212> TYPE: DNA
<213> ORGANISM: Artificial Sequence
<220> FEATURE:
<223> OTHER INFORMATION: Synthetic primer: SK918

<400> SEQUENCE: 23
ctgatatcga tcgagtcgaa ctgtcgcttc                                       30

<210> SEQ ID NO 24
<211> LENGTH: 28
<212> TYPE: DNA
<213> ORGANISM: Artificial Sequence
<220> FEATURE:
<223> OTHER INFORMATION: Synthetic primer: SK949

<400> SEQUENCE: 24
gtttcgcatg gcgcgcctga gacaatgg                                         28

<210> SEQ ID NO 25
<211> LENGTH: 32
<212> TYPE: DNA
<213> ORGANISM: Artificial Sequence
<220> FEATURE:
<223> OTHER INFORMATION: Synthetic primer: SK946

<400> SEQUENCE: 25
cacaggcgcg ccgatcgcca tcccgtcgcg tc                                    32

<210> SEQ ID NO 26
<211> LENGTH: 41
<212> TYPE: DNA
<213> ORGANISM: Artificial Sequence
<220> FEATURE:
<223> OTHER INFORMATION: Synthetic primer: MC40

<400> SEQUENCE: 26
ctatgacatg ccctgaggcg atgctggcca ggtacgagct g                          41

<210> SEQ ID NO 27
<211> LENGTH: 45
<212> TYPE: DNA
<213> ORGANISM: Artificial Sequence
<220> FEATURE:
<223> OTHER INFORMATION: Synthetic primer: MC41

<400> SEQUENCE: 27
cagcctcgcg gtcacagtga gaggaacggg gtgaagtcgt ataag                      45

<210> SEQ ID NO 28
<211> LENGTH: 34
<212> TYPE: DNA
<213> ORGANISM: Artificial Sequence
<220> FEATURE:
<223> OTHER INFORMATION: Synthetic primer: SK1008

<400> SEQUENCE: 28
ctagcgatcg cgtgtgcaca taggtgagtt ctcc                                  34

<210> SEQ ID NO 29
```

<211> LENGTH: 34
<212> TYPE: DNA
<213> ORGANISM: Artificial Sequence
<220> FEATURE:
<223> OTHER INFORMATION: Synthetic primer: SK1009

<400> SEQUENCE: 29
ctagcgatcg cgcagactgg catgcctcaa tcac            34

<210> SEQ ID NO 30
<211> LENGTH: 25
<212> TYPE: DNA
<213> ORGANISM: Artificial Sequence
<220> FEATURE:
<223> OTHER INFORMATION: Synthetic primer: MC 42

<400> SEQUENCE: 30
ctcgccatct gacaacctac aaatc                       25

<210> SEQ ID NO 31
<211> LENGTH: 26
<212> TYPE: DNA
<213> ORGANISM: Artificial Sequence
<220> FEATURE:
<223> OTHER INFORMATION: Synthetic primer: MC 48

<400> SEQUENCE: 31
ctagtaccct gagttgtctc gcctcc                      26

<210> SEQ ID NO 32
<211> LENGTH: 25
<212> TYPE: DNA
<213> ORGANISM: Artificial Sequence
<220> FEATURE:
<223> OTHER INFORMATION: Synthetic primer: MC 45

<400> SEQUENCE: 32
cctctaccat aacaggatcc atctg                       25

<210> SEQ ID NO 33
<211> LENGTH: 28
<212> TYPE: DNA
<213> ORGANISM: Artificial Sequence
<220> FEATURE:
<223> OTHER INFORMATION: Synthetic primer: MC 50

<400> SEQUENCE: 33
cgtgagctga tgaaggagag aacaaagg                    28

<210> SEQ ID NO 34
<211> LENGTH: 44
<212> TYPE: DNA
<213> ORGANISM: Artificial Sequence
<220> FEATURE:
<223> OTHER INFORMATION: Synthetic oligonucleotide: E121T

<400> SEQUENCE: 34
tccaccacca gcagaacctc accaaggccg acccctctt ccac   44

<210> SEQ ID NO 35
<211> LENGTH: 44
<212> TYPE: DNA
<213> ORGANISM: Artificial Sequence
<220> FEATURE:
<223> OTHER INFORMATION: Synthetic oligonucleotide: E121T-r

<400> SEQUENCE: 35
gtggaagagg gggtcggcct tggtgaggtt ctgctggtgg tgga           44

<210> SEQ ID NO 36
<211> LENGTH: 42
<212> TYPE: DNA
<213> ORGANISM: Artificial Sequence
<220> FEATURE:
<223> OTHER INFORMATION: Synthetic oligonucleotide: P394N

<400> SEQUENCE: 36
agaccgccga gggctactgc aacctcagca ccttcacccg cg             42

<210> SEQ ID NO 37
<211> LENGTH: 42
<212> TYPE: DNA
<213> ORGANISM: Artificial Sequence
<220> FEATURE:
<223> OTHER INFORMATION: Synthetic oligonucleotide: P394N-r

<400> SEQUENCE: 37
cgcgggtgaa ggtgctgagg ttgcagtagc cctcggcggt ct             42

<210> SEQ ID NO 38
<211> LENGTH: 41
<212> TYPE: DNA
<213> ORGANISM: Artificial Sequence
<220> FEATURE:
<223> OTHER INFORMATION: Synthetic oligonucleotide: D386N

<400> SEQUENCE: 38
tcaagatccc cggctgcaac aaccagaccg ccgagggcta c              41

<210> SEQ ID NO 39
<211> LENGTH: 41
<212> TYPE: DNA
<213> ORGANISM: Artificial Sequence
<220> FEATURE:
<223> OTHER INFORMATION: Synthetic oligonucleotide: D386N-r

<400> SEQUENCE: 39
gtagccctcg gcggtctggt tgttgcagcc ggggatcttg a              41

<210> SEQ ID NO 40
<211> LENGTH: 46
<212> TYPE: DNA
<213> ORGANISM: Artificial Sequence
<220> FEATURE:
<223> OTHER INFORMATION: Synthetic oligonucleotide: K202NN204T

<400> SEQUENCE: 40
cccagcaagc tcagcatcaa cgacaccggc aacgaggtct ccctcg         46

<210> SEQ ID NO 41
<211> LENGTH: 46
<212> TYPE: DNA
<213> ORGANISM: Artificial Sequence
<220> FEATURE:
<223> OTHER INFORMATION: Synthetic oligonucleotide: K202NN204T-r

<400> SEQUENCE: 41
cgagggagac ctcgttgccg gtgtcgttga tgctgagctt gctggg         46

<210> SEQ ID NO 42
<211> LENGTH: 48
<212> TYPE: DNA

```
<213> ORGANISM: Artificial Sequence
<220> FEATURE:
<223> OTHER INFORMATION: Synthetic oligonucleotide: Q151NP153S

<400> SEQUENCE: 42
aggccgtcga gaaggaggcc aacaccagca tcgacaacct caaccagc            48

<210> SEQ ID NO 43
<211> LENGTH: 48
<212> TYPE: DNA
<213> ORGANISM: Artificial Sequence
<220> FEATURE:
<223> OTHER INFORMATION: Synthetic oligonucleotide: Q151NP153S-r

<400> SEQUENCE: 43
gctggttgag gttgtcgatg ctggtgttgg cctccttctc gacggcct            48

<210> SEQ ID NO 44
<211> LENGTH: 44
<212> TYPE: DNA
<213> ORGANISM: Artificial Sequence
<220> FEATURE:
<223> OTHER INFORMATION: Synthetic oligonucleotide: BP17P373T

<400> SEQUENCE: 44 ccccctcag cctcaaccag accgccggca gcgtccagct caag                 44

<210> SEQ ID NO 45
<211> LENGTH: 44
<212> TYPE: DNA
<213> ORGANISM: Artificial Sequence
<220> FEATURE:
<223> OTHER INFORMATION: Synthetic oligonucleotide: BP17P373T-r

<400> SEQUENCE: 45
cttgagctgg acgctgccgg cggtctggtt gaggctgagg gggg                44

<210> SEQ ID NO 46
<211> LENGTH: 41
<212> TYPE: DNA
<213> ORGANISM: Artificial Sequence
<220> FEATURE:
<223> OTHER INFORMATION: Synthetic oligonucleotide: BP17R76N

<400> SEQUENCE: 46
agcagcaggg catcctcagc aacggctcgt gccccacccc c                   41

<210> SEQ ID NO 47
<211> LENGTH: 41
<212> TYPE: DNA
<213> ORGANISM: Artificial Sequence
<220> FEATURE:
<223> OTHER INFORMATION: Synthetic oligonucleotide: BP17R76N-r

<400> SEQUENCE: 47
gggggtgggg cacgagccgt tgctgaggat gccctgctgc t                   41
```

What is claimed is:

1. A phytase polypeptide comprising SEQ ID NO: 1 and variants at least 90% identical thereto having increased glycosylation when compared to a control phytase lacking increased glycosylation, and made in a deglycosylation-deficient filamentous fungus, wherein said phytase has increased stability and pelleting stability when compared to a phytase made in a filamentous fungus that is not deglycosylation-deficient.

2. The phytase polypeptide of claim 1 comprising one or more of the following substitutions: E121T, P394N, D386N, K202N and N204T, Q151N and P153S, P373T, Q76N with reference to the position numbering of SEQ ID NO:1.

3. The phytase polypeptide of claim 2 wherein said polypeptide has the amino acid sequence of SEQ NOs 5, 6, 7, 8, 9, 10 or 11.

4. The phytase polypeptide of claims 1 or 3 having 1 or more added glycosylation sites.

5. The phytase polypeptide of claim 4 wherein the stability comprises increased inactivity reversibility following exposure to an elevated temperature as compared to a control phytase lacking increased glycosylation, wherein the elevated temperature is at least 80° C.

6. The phytase of claim 5 wherein the inactivity reversibility is at least 1% higher than a control phytase lacking increased glycosylation.

7. The phytase of claim 6 wherein the inactivity reversibility occurs after processing into a food or feed pellet.

8. The phytase polypeptide of claim 7 wherein the stability comprises increased recovered activity following exposure to an elevated temperature of at least 80° C. as compared to a control phytase lacking the increased glycosylation.

9. The phytase of claim 8 wherein the increased recovered activity as compared to a control phytase lacking increased glycosylation is at least 20%.

10. The phytase polypeptide of claim 7 wherein the stability comprises recovered activity following exposure to an elevated temperature of at least 80° C., as compared to the phytase prior to the exposure at the elevated temperature.

11. The phytase of claim 10 wherein the recovered activity is at least 40%, as compared to the phytase prior to the exposure at the elevated temperature.

12. The phytase polypeptide according to claim 11 wherein the increased recovered activity occurs after processing into a food or feed pellet.

13. The phytase polypeptide according to claim 1, wherein the filamentous fungus is an *Aspergillus* spp., a *Fusarium* spp., a *Myceliophthora* spp., or a *Trichoderma* spp.

14. The phytase polypeptide according to claim 13, wherein the *Aspergillus* is *A. niger, A. oryzae, A. nidulans, A. tubingensis*, or *A. awamori*.

15. The phytase polypeptide according to claim 13, wherein the *Trichoderma* is *T. reesei*.

16. The phytase polypeptide according to claim 1 wherein the phytase is contained in a granule, optionally wherein the granule is a multi-layered granule, optionally wherein the granule is contained in a pellet, and optionally wherein the pellet is contained in an animal feed.

* * * * *